(12) United States Patent
Hirano

(10) Patent No.: US 12,252,483 B2
(45) Date of Patent: Mar. 18, 2025

(54) METHOD FOR PRODUCING OPTICALLY ACTIVE 1, 4-BENZOTHIAZEPINE-1-OXIDE DERIVATIVE

(71) Applicant: AETAS PHARMA CO., LTD., Tokyo (JP)

(72) Inventor: Sayuri Hirano, Osaka (JP)

(73) Assignee: AETAS PHARMA CO., LTD., Tokyo (JP)

( * ) Notice: Subject to any disclaimer, the term of this patent is extended or adjusted under 35 U.S.C. 154(b) by 609 days.

(21) Appl. No.: 17/628,979

(22) PCT Filed: Jul. 22, 2020

(86) PCT No.: PCT/JP2020/028375
§ 371 (c)(1),
(2) Date: May 17, 2022

(87) PCT Pub. No.: WO2021/015221
PCT Pub. Date: Jan. 28, 2021

(65) Prior Publication Data
US 2022/0324856 A1 Oct. 13, 2022

(30) Foreign Application Priority Data
Jul. 22, 2019 (JP) .................................. 2019-134766

(51) Int. Cl.
*C07D 417/06* (2006.01)
(52) U.S. Cl.
CPC .................................. *C07D 417/06* (2013.01)
(58) Field of Classification Search
CPC .................................................. C07D 417/06
See application file for complete search history.

(56) References Cited

U.S. PATENT DOCUMENTS

| | | |
|---|---|---|
| 2005/0187386 A1 | 8/2005 | Marks et al. |
| 2007/0049572 A1 | 3/2007 | Marks et al. |
| 2011/0306594 A1 | 12/2011 | Kaneko et al. |
| 2017/0247362 A1* | 8/2017 | Kaneko ................ A61K 31/554 |

FOREIGN PATENT DOCUMENTS

| | | |
|---|---|---|
| JP | 2008-534497 A | 8/2008 |
| JP | 2009-506034 A | 2/2009 |
| JP | 2010-195759 A | 9/2010 |
| JP | 2012-46430 A | 3/2012 |
| JP | 2012-131710 A | 7/2012 |
| WO | 2007/024717 A2 | 3/2007 |
| WO | 2010/098080 A1 | 9/2010 |
| WO | 2010/114563 A1 | 10/2010 |
| WO | 2016/017448 A1 | 2/2016 |

OTHER PUBLICATIONS

Makino et al., "Catalytic asymmetric S-oxidation of N-benzoyl-1,5-benzothiazepines", Tetrahedron Letters, 2017, vol. 58, pp. 2885-2888, (4 pages).
Song et al., "An efficient asymmetric synthesis of an estrogen receptor modulator by sulfoxide-directed borane reduction", PNAS, Apr. 20, 2004, vol. 101, No. 16, pp. 5776-5781, (6 pages).
International Search Report dated Aug. 25, 2020, issued in counterpart International Application No. PCT/JP2020/028375 (4 pages).

* cited by examiner

*Primary Examiner* — Timothy R Rozof
(74) *Attorney, Agent, or Firm* — WHDA, LLP

(57) ABSTRACT

The present invention addresses the problem of providing an efficient asymmetric synthesis method for an optically active 1,4-benzothiazepine-1-oxide derivative.
[Solution] According to the present invention, an optically active 1,4-benzothiazepine-1-oxide derivative is efficiently produced by reacting a 1,4-benzothiazepine derivative or a salt thereof with a reagent containing a titanium compound, a chiral diol compound and water, and an oxidant in a solvent.

18 Claims, 3 Drawing Sheets

[FIG. 1]
Dynamic vapor sorption (DVS) isotherm plot of hydrochloride of the compound of Formula (IV'-a)
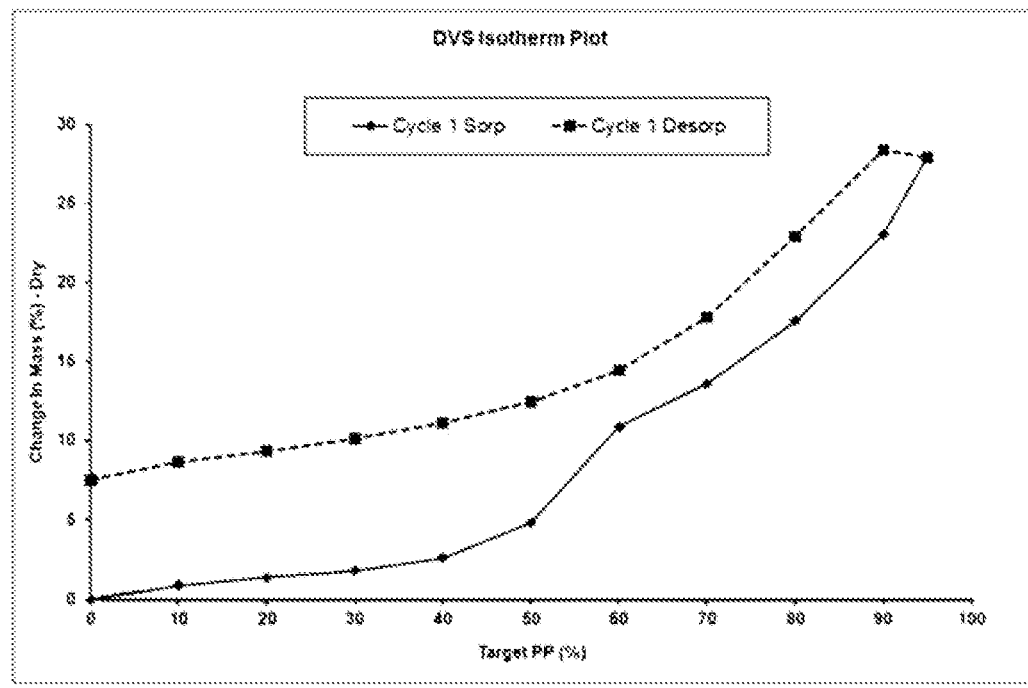

[FIG. 2]
Dynamic vapor sorption (DVS) isotherm plot of p-toluenesulfonate of the compound of Formula (IV'-a)
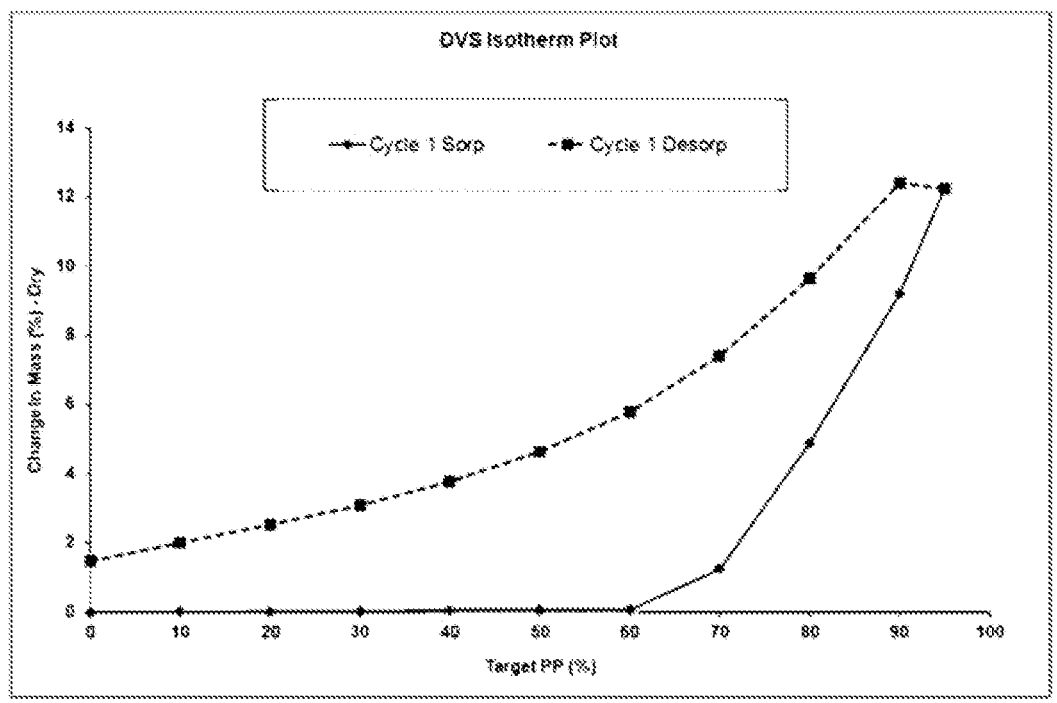

[FIG. 3]
Dynamic vapor sorption (DVS) isotherm plot of (R)-mandelate of the compound of Formula (IV'-a)
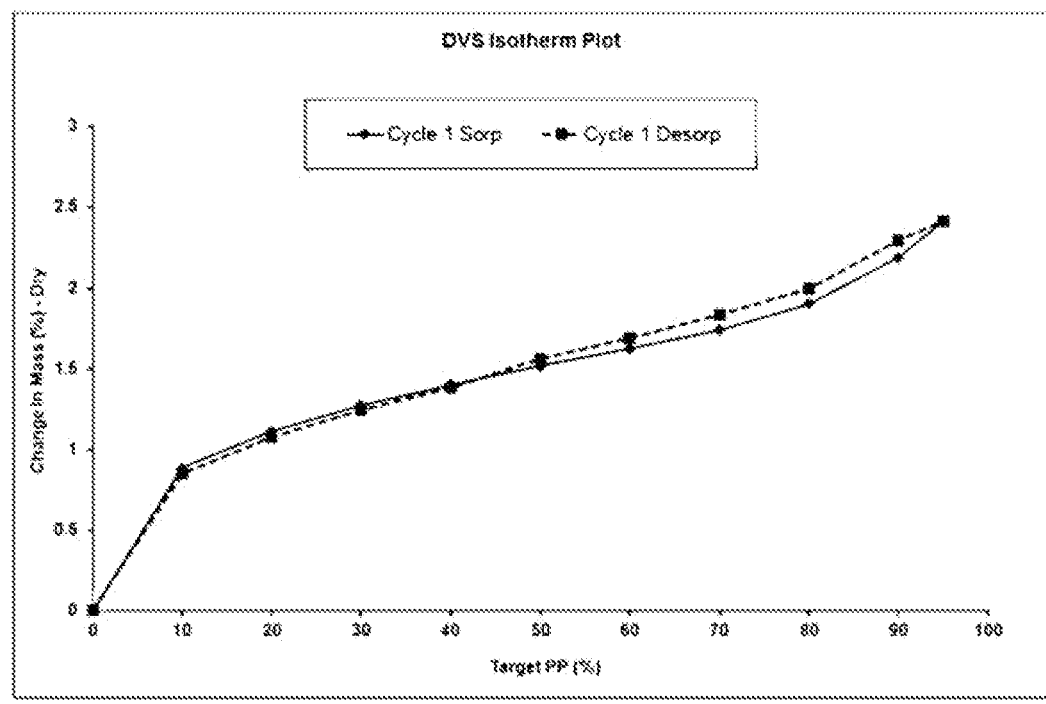

METHOD FOR PRODUCING OPTICALLY ACTIVE 1, 4-BENZOTHIAZEPINE-1-OXIDE DERIVATIVE

TECHNICAL FIELD

The present invention relates to a method for producing an optically active 1,4-benzothiazepine-1-oxide derivative, and a salt of the optically active 1,4-benzothiazepine-1-oxide derivative.

BACKGROUND ART

Patent Document 1 discloses that one isomer (first optical isomer component) of optical isomers of 1,4-benzothiazepine-1-oxide derivatives slowly increases heart rate and blood pressure, and is useful as a therapeutic or preventive agent for atrial fibrillation or heart failure. In addition, it is also disclosed that the enantiomer (second optical isomer component) has opposite pharmacological actions and decreases the heart rate and blood pressure.

Patent Document 1 and Patent Document 2 disclose a method for producing a 1,4-benzothiazepine-1-oxide derivative as a sulfoxide substance by allowing meta-chloroperbenzoic acid (mCPBA) as an oxidant to act on a sulfur atom of a heterocyclic ring of the 1,4-benzothiazepine derivative.

In addition, Patent Document 1 discloses a method for optically resolving a racemate of a 1,4-benzothiazepine-1-oxide derivative using a chiral column, and separating a first component and a second component of the optical isomer, respectively. However, in the optical resolution by the chiral column, it is necessary to discard unnecessary enantiomers, and it is difficult to improve the total yield of all processes. In addition, for the purpose of producing a specific optical isomer by scaling-up, the method using a chiral column is not an industrially satisfactory method in terms of equipment.

Further, Patent Document 1 discloses a hydrochloride as a salt of 4-[3-(4-benzylpiperidin-1-yl)propionyl]-7-methoxy-2,3,4,5-tetrahydro-1,4-benzothiazepine-1-oxide. It is generally known that a compound in a hydrochloride form tends to have high hygroscopicity, but Patent Document 1 does not disclose a crystal or hygroscopicity of a hydrochloride of 4-[3-(4-benzylpiperidin-1-yl)propionyl]-7-methoxy-2,3,4,5-tetrahydro-1,4-benzothiazepine-1-oxide.

Patent Document 3 discloses JTV-519 which is a 1,4-benzothiazepine derivative, and S23 which is a dioxide ($SO_2$) form thereof. It is also disclosed that S23 is obtained by oxidizing JTV-519 with hydrogen peroxide. However, Patent Document 3 does not specifically disclose the oxidation reaction. Further, there is no specific disclosure about the production of an oxide of a sulfoxide substance rather than a dioxide substance, and naturally, there is no description about an asymmetric synthesis reaction of an optically active sulfoxide substance.

Several methods are known for asymmetric oxidation of sulfides.

One of the methods is a method for producing an optically active sulfoxide from a sulfide using a complex containing a transition metal-containing compound and an optically active ligand as a catalyst. However, there is no example of oxidizing a sulfur atom of benzothiazepine, and the present inventors were not able to find an example of oxidizing a sulfur atom existing in a heterocyclic ring in the first place. Since there is no reference example for asymmetric oxidation of a 1,4-benzothiazepine derivative, and a chiral complex containing a transition metal to be a catalyst is relatively expensive, it was considered difficult to establish an industrial production method of a 1,4-benzothiazepine-1-oxide derivative using the catalyst.

As another method, an asymmetric oxidation method using a reactant (Kagan's Reagent) containing a titanium compound and a diol ligand is known, but also in this method, an example in which a sulfur atom present in a heterocyclic ring is oxidized is extremely rare. The present inventors referred to a report in which the asymmetric oxidation of a 1,5-benzothiazepine derivative was attempted (Non-Patent Document 1). However, the document reported that a substituent $R^1$ present at a 9-position of a 1,5-benzothiazepine ring contributes to an enantioselective oxidation reaction of sulfides. On the other hand, since the 1,4-benzothiazepine derivative handled by the present inventors does not have a substituent at the 9-position of the benzothiazepine ring, it was understood that it is not appropriate to directly apply the method described in the Document.

CITATION LIST

Patent Document

Patent Document 1: WO 2016/017448 A
Patent Document 2: WO 2010/098080 A
Patent Document 3: WO 2007/024717 A

Non-Patent Document

Non-Patent Document 1: Makino K et al., Tetrahedron Lett., 2017, Vol. 58, pp. 2885-88
Non-Patent Document 2: Song Z J et al., PNAS, 2004, Vol. 101, pp. 5776-81

SUMMARY OF THE INVENTION

Problems to be Solved by the Invention

An object of the present invention is to provide an efficient asymmetric synthesis method of an optically active 1,4-benzothiazepine-1-oxide derivative.

Another object of the present invention is to provide a salt (salt having low hygroscopicity) having excellent physical properties of (R)-4-[3-(4-benzylpiperidin-1-yl)propionyl]-7-methoxy-2,3,4,5-tetrahydro-1,4-benzothiazepine-1-oxide.

Means for Solving the Problems

The present inventors have referred to a document in which a sulfur atom of a 1,4-benzoxathiine derivative that is a heterocyclic compound is asymmetrically oxidized (Non-Patent Document 2), and tried to apply the reaction system of Kagan disclosed in the document. However, when 4-[3-(4-benzylpiperidin-1-yl)propionyl]-7-methoxy-2,3,4,5-tetrahydro-1,4-benzothiazepine was used as a substrate, it was not possible to achieve a desired enantioselective oxidation reaction. Therefore, as a result of further intensive studies to solve the above problems, the present inventors have found that an optically active 1,4-benzothiazepine-1-oxide derivative can be efficiently produced by reacting a 1,4-benzothiazepine derivative in a solvent under an appropriate operation in the presence of a reactant containing a titanium compound, a chiral diol compound, and water and an oxidant. In addition, the present inventors have also found a salt of (R)-4-[3-(4-benzylpiperidin-1-yl)propionyl]-7- methoxy-2,3,4,5-tetrahydro-1,4-benzothiazepine-1-oxide having low hygroscopicity, and completed the present invention.

That is, specific aspects of the present invention may include the following [1] to [37].

[1] A method for producing an optically active compound of the Formula (II) or a salt thereof

[Chem. 2]

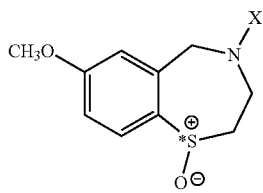

(II)

wherein * indicates the presence of optical isomers, and X represents a hydrogen atom or a substituent,
wherein the method comprises the following processes:
a process of allowing a compound of the Formula (I) or a salt thereof to react with a reactant containing a titanium compound, a chiral diol compound, and water, and an oxidant in a solvent,

[Chem. 1]

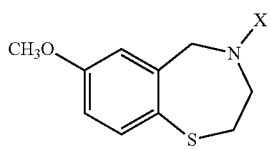

(I)

wherein X represents a hydrogen atom or a substituent.

[2] The method according to the above [1], wherein the compound of the Formula (I) or the salt thereof is a compound of the Formula (I).

[3] The method according to the above [1], wherein the compound of the Formula (I) or the salt thereof is hydrochloride, fumarate, mandelate, or sulfonate of the compound of the Formula (I).

[4] The method according to the above [1], wherein the compound of the Formula (I) or the salt thereof is a compound of the Formula (III) and a salt thereof,

[Chem. 3]

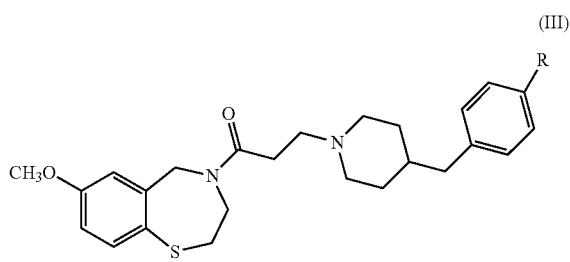

(III)

wherein, R represents a hydrogen atom or a hydroxyl group,
wherein the compound of the Formula (II) or the salt thereof is an optically active compound of the Formula (IV) or a salt thereof,

[Chem. 4]

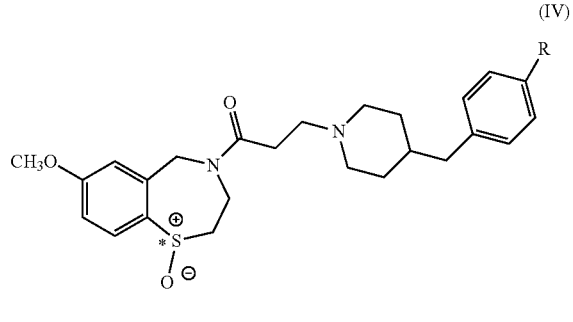

(IV)

wherein, * indicates the presence of optical isomers, and R represents a hydrogen atom or a hydroxyl group.

[5] The method according to the above [4], wherein in the Formula (III) and Formula (IV), R is a hydrogen atom.

[6] The method according to the above [4] or [5], wherein the compound of the Formula (III) or the salt thereof is the compound of the Formula (III).

[7] The method according to the above [4] or [5], wherein the compound of the Formula (III) or the salt thereof is a hydrochloride, fumarate, mandelate, or sulfonate of the compound of the Formula (III).

[8] The method according to any one of the above [1] to [7], wherein the titanium compound is titanium tetraisopropoxide.

[9] The production method according to any one of the above [1] to [8], wherein the diol compound is tartaric acid diester having the Formula (V-a) or (V-b):

[Chem. 5]

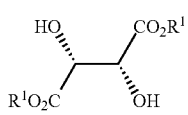

(V-a)

wherein $R^1$ represents an optionally substituted $C_{2-6}$ alkyl group or benzyl, or

[Chem. 6]

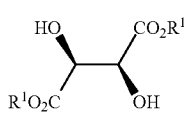

(V-b)

wherein $R^1$ is as defined above.

[10] The method according to the above [9], wherein the tartaric acid diester of the Formula (V-a) or (V-b) is tartaric acid diester selected from the group consisting of diethyl tartarate, diisopropyl tartarate, and dibenzyl tartarate.

[11] The method according to any one of the above [1] to [10], wherein the oxidant is a t-butyl hydroperoxide aqueous solution or cumene hydroperoxide.

[12] The method according to the above [11], wherein the oxidant is cumene hydroperoxide.

[13] The method according to any one of the above [1] to [12], wherein the solvent is a solvent selected from the group consisting of toluene, trichloromethane, and ethyl acetate.

[14] The method according to the above [13], wherein the solvent is toluene.

[15] A mandelate of an optically active compound having the following Formula (VI),

[Chem. 7]

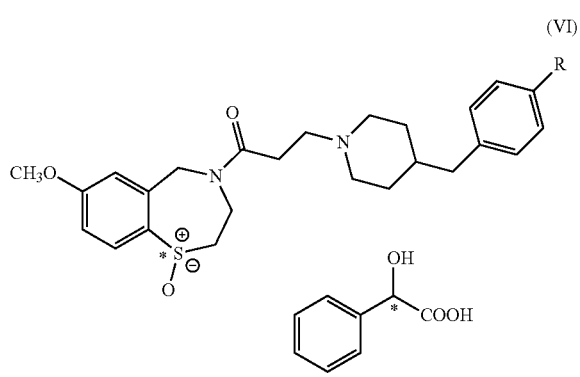

(VI)

wherein, * indicates the presence of optical isomers, and R represents a hydrogen atom or a hydroxyl group.

[16] The mandelate of the optically active compound according to the above [15], wherein in the Formula (VI), R is a hydrogen atom.

[17] A sulfonate of an optically active compound having the following Formula (VII),

[Chem. 8]

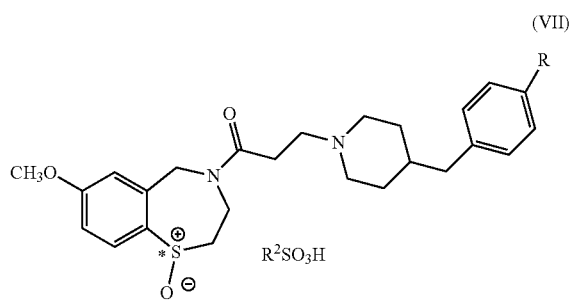

(VII)

wherein, $R^2$ represents an optionally substituted hydrocarbon group, * indicates the presence of optical isomers, and R represents a hydrogen atom or a hydroxyl group.

[18] The sulfonate of the optically active compound according to the above [17], wherein the sulfonate is p-toluenesulfonate or methanesulfonate.

[19] The sulfonate of the optically active compound according to the above [17] or [18], wherein R is a hydrogen atom.

[20] A method for producing hydrochloride of an optically active compound having the following Formula (VIII), the method comprises a process of mixing a salt of an optically active compound having the following Formula (IV), which is selected from the group consisting of fumarate, mandelate, p-toluenesulfonic acid, and methanesulfonate with a solution containing hydrogen chloride in a solvent,

[Chem. 4]

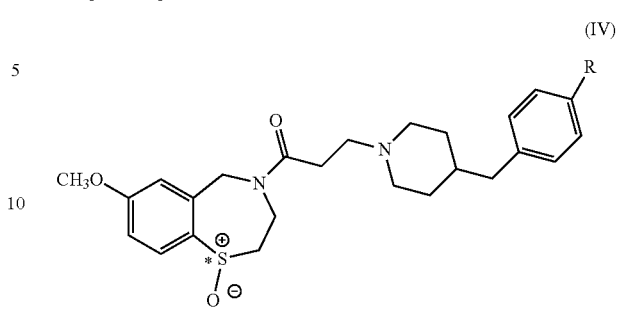

(IV)

wherein, * indicates the presence of optical isomers, and R represents a hydrogen atom or a hydroxyl group, and

[Chem. 9]

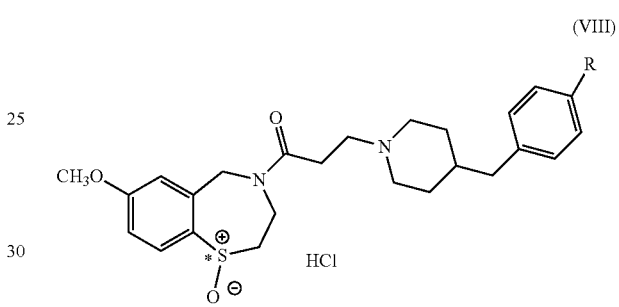

(VIII)

wherein, * indicates the presence of optical isomers, and R represents a hydrogen atom or a hydroxyl group.

[21] The method according to the above [20], wherein R is a hydrogen atom.

[22] The method according to the above [20] or [21], wherein the solvent is tetrahydrofuran, acetonitrile, ethyl acetate, or a mixture of two or more kinds among the three kinds.

[23] The method according to the above [22], wherein the solvent is ethyl acetate, a mixture of ethyl acetate and acetonitrile, or a mixture of tetrahydrofuran and acetonitrile.

[24] The method according to the above [23], wherein the solvent is a mixture of tetrahydrofuran and acetonitrile.

[25] The method according to any one of the above [20] to [24], wherein the solution containing hydrogen chloride is methanol, ethanol, or ethyl acetate.

[26] The method according to the above [25], wherein the solution containing the hydrogen chloride is the ethyl acetate.

[27] The method according to any one of the above [20] to [26], wherein the hydrogen chloride contained in a solution containing the optically active compound of the Formula (IV) and hydrochloric acid is used at an equivalent ratio of 1:1.1 to 1:1.5.

[28] The method according to any one of the above [20] to [27], wherein the salt selected from the group consisting of fumarate, mandelate, p-toluenesulfonate, and methanesulfonate is mandelate.

[29] The method according to the above [28], wherein the mandelate is (R)-mandelate.

[30] The method according to any one of the above [1] to [14], wherein the optically active compound is an (R)-form optically active compound.

[31] The method according to any one of the above [1] to [14], wherein the optically active compound is an (S)-form optically active compound.

[32] The mandelate of the optically active compound according to the above [15] or [16], wherein the optically active compound is an (R)-form optically active compound.

[33] The mandelate of the optically active compound according to the above [15] or [16], wherein the optically active compound is an (S)-form optically active compound.

[34] The sulfonate of the optically active compound according to any one of the above [17] to [19], wherein the optically active compound is an (R)-form optically active compound.

[35] The sulfonate of the optically active compound according to any one of the above [17] to [19], wherein the optically active compound is an (S)-form optically active compound.

[36] The method according to any one of the above [20] to [29], wherein the optically active compound is an (R)-form optically active compound.

[37] The method according to any one of the above [20] to [28], wherein the optically active compound is an (S)-form optically active compound.

Effects of the Invention

According to the present invention, an optically active 1,4-benzothiazepine-1-oxide derivative can be produced efficiently, with high purity and further with high yield.

In the asymmetric oxidation method of sulfur atoms, it has been reported that the enantiomeric excess is remarkably improved by adding diisopropylethylamine to the reaction system (for example, Non-Patent Document 2), but the method of the present invention can achieve an asymmetric oxidation reaction showing a high enantiomeric excess (high optical purity) without adding a base such as diisopropylethylamine. It is an advantage of the method of the present invention that diisopropylethylamine, which is skin irritating and flammable and requires careful handling, is not required for the reaction. In addition, as compared with the case where diisopropylethylamine is present in the reaction system and the case where diisopropylethylamine is not present in the reaction system, the latter case can be performed more quickly and easily as the subsequent process of separating and purifying a desired product (for example, a compound represented by Formula (IV'-a) or a salt thereof) from the reaction mixture after completion of the oxidation reaction. That is, the method of the present invention that does not use diisopropylethylamine is excellent in rapidity, convenience, and safety, and achieves a reaction at low cost.

According to the present invention, it is possible to provide a salt (salt having low hygroscopicity) having excellent physical properties of (R)-4-[3-(4-benzylpiperidin-1-yl)propionyl]-7-methoxy-2,3,4,5-tetrahydro-1,4-benzothiazepine.

BRIEF DESCRIPTION OF DRAWINGS

FIG. 1 illustrates a dynamic vapor sorption (DVS) isotherm plot of hydrochloride of (R)-4-[3-(4-benzylpiperidin-1-yl)propionyl]-7-methoxy-2,3,4,5-tetrahydro-1,4-benzothiazepine-1-oxide.

FIG. 2 illustrates a dynamic vapor sorption (DVS) isotherm plot of p-toluenesulfonate of (R)-4-[3-(4-benzylpiperidin-1-yl)propionyl]-7-methoxy-2,3,4,5-tetrahydro-1,4-benzothiazepine-1-oxide.

FIG. 3 illustrates a dynamic vapor sorption (DVS) isotherm plot of (R)-mandelate of (R)-4-[3-(4-benzylpiperidin-1-yl)propionyl]-7-methoxy-2,3,4,5-tetrahydro-1,4-benzothiazepine-1-oxide.

DESCRIPTION OF EMBODIMENTS

Modes for carrying out the present invention will be described below.

The compounds having Formulae (I), (II), (III), (III'), (IV), (IV'), (IV'-a), (IV'-b), and the like, and the definitions of the symbols in the formulae will be described in detail below.

The compound having the following Formula (I) is a 1,4-benzothiazepine derivative used as a substrate in the method for producing an optically active 1,4-benzothiazepine-1-oxide derivative (compound having the following Formula (II)) of the present invention.

[Chem. 1]

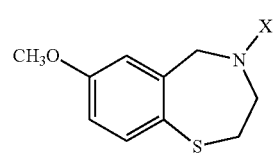

(I)

[Chem. 2]

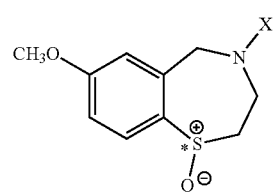

(II)

In the Formula (I) and Formula (II), X represents a hydrogen atom or a substituent.

Examples of the "substituent" represented by X include a formyl group, a carboxy group, a $C_{1-6}$ alkyl-carbonyl group, a $C_{2-6}$ alkenyl-carbonyl group (for example, acryloyl, crotonoyl), a $C_{3-10}$ cycloalkyl-carbonyl group (for example, cyclobutanecarbonyl, cyclopentanecarbonyl, cyclohexanecarbonyl, and cycloheptanecarbonyl), a $C_{3-10}$ cycloalkenyl-carbonyl group (for example, 2-cyclohexenecarbonyl), a $C_{6-14}$ aryl-carbonyl group, and a $C_{7-16}$ aralkyl-carbonyl group; those having the following Formula (IX),

[Chem. 10]

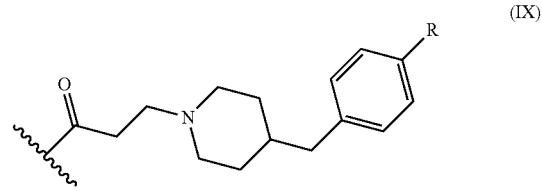

(IX)

wherein, R represents a hydrogen atom or a hydroxyl group;

and those having the following Formula (X),

[Chem. 11]

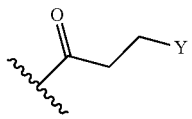

(X)

wherein Y represents a leaving group.

Examples of the leaving group represented by Y include a halogen atom; an optionally halogenated $C_{1-6}$ alkylsulfonyloxy group such as methanesulfonyloxy, ethanesulfonyloxy, trichloromethanesulfonyloxy, or trifluoromethanesulfonyloxy; an optionally substituted $C_{6-10}$ arylsulfonyloxy group such as phenylsulfonyloxy, m-nitrophenylsulfonyloxy, p-toluenesulfonyloxy, or naphthylsulfonyloxy (for example, a $C_{6-10}$ arylsulfonyloxy group optionally having 1 to 3 substituents selected from a $C_{1-6}$ alkyl group, a $C_{1-6}$ alkoxy group, and a nitro group); and an optionally halogenated acyloxy group such as trichloroacetoxy and trifluoroacetoxy.

Y is particularly preferably a halogen atom.

X is particularly preferably a substituent having the Formula (IX).

R is preferably a hydrogen atom.

A preferred example of the Formula (I) is a compound having the following Formula (III).

[Chem. 3]

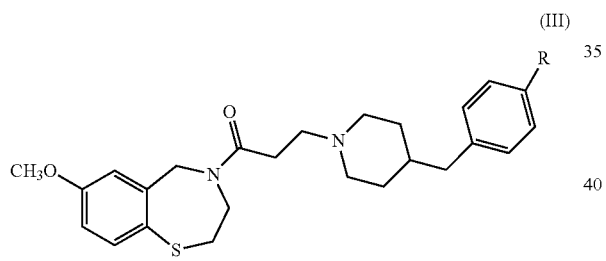

(III)

wherein, R represents a hydrogen atom or a hydroxyl group.

In the compound represented by the Formula (III), more preferably, a compound having the following Formula (III'), that is, 4-[3-(4-benzylpiperidin-1-yl)propionyl]-7-methoxy-2,3,4,5-tetrahydro-1,4-benzothiazepine can be exemplified.

[Chem. 12]

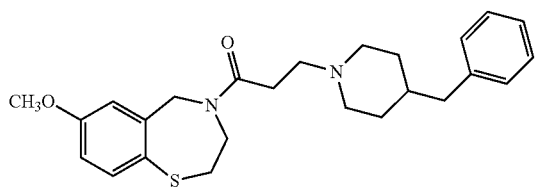

(III')

Preferred examples of the compound of the Formula (II) which is a product of the method of the present invention are compounds having the following Formula (IV).

[Chem. 4]

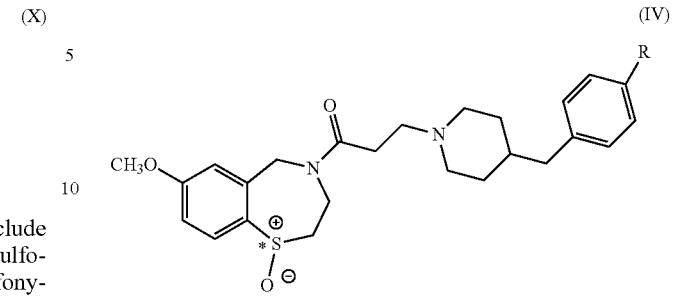

(IV)

wherein, * indicates the presence of optical isomers, and R represents a hydrogen atom or a hydroxyl group.

More preferred examples of the compound of the Formula (II) include a compound having the following Formula (IV'), that is, 4-[3-(4-benzylpiperidin-1-yl)propionyl]-7-methoxy-2,3,4,5-tetrahydro-1,4-benzothiazepine-1-oxide.

[Chem. 13]

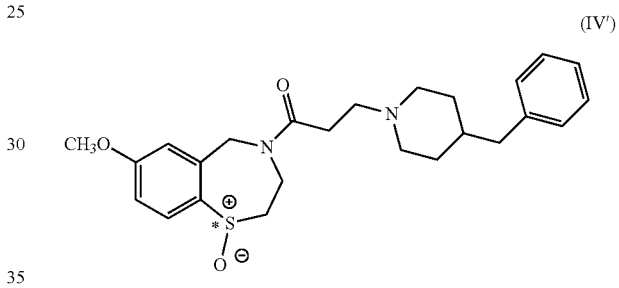

(IV')

wherein, * indicates the presence of optical isomers.

An example of the compound of the Formula (IV') is a compound having the following Formula (IV'-a), that is, (R)-4-[3-(4-benzylpiperidin-1-yl)propionyl]-7-methoxy-2,3,4,5-tetrahydro-1,4-benzothiazepine-1-oxide.

[Chem. 14]

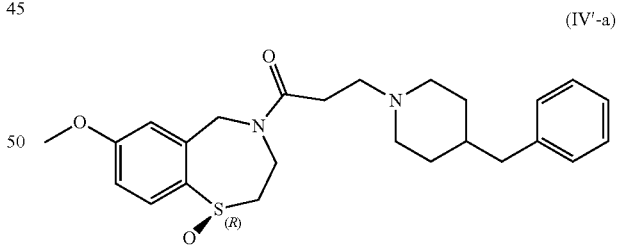

(IV'-a)

The analysis by the present inventors has revealed that (R)-4-[3-(4-benzylpiperidin-1-yl)propionyl]-7-methoxy-2,3,4,5-tetrahydro-1,4-benzothiazepine-1-oxide is the same compound as the "first optical isomer component of the compound of the Formula [IV]" in Patent Document 1. The compound has the properties of slowly increasing a heart rate and a blood pressure and improving hemodynamics, and is useful as a medicine for improving heart failure or the like.

Another example of the compound of the Formula (IV') is a compound having the following Formula (IV'-b), that is, (S)-4-[3-(4-benzylpiperidin-1-yl)propionyl]-7-methoxy-2,3,4,5-tetrahydro-1,4-benzothiazepine-1-oxide.

[Chem. 15]

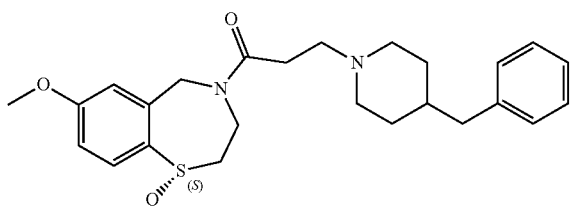

(IV'-b)

The analysis by the present inventors has revealed that (S)-4-[3-(4-benzylpiperidin-1-yl)propionyl]-7-methoxy-2,3,4,5-tetrahydro-1,4-benzothiazepine-1-oxide is the same compound as the "second optical isomer component of the compound of the Formula [IV]" in Patent Document 1.

The compound of the Formula (IV'-a) and the compound of the Formula (IV'-b) can be separated and identified, for example, by the method disclosed in Patent Document 1.

A particularly preferred example of the compound of the Formula (IV') is (R)-4-[3-(4-benzylpiperidin-1-yl)propionyl]-7-methoxy-2,3,4,5-tetrahydro-1,4-benzothiazepine-1-oxide having the Formula (IV'-a).

The compounds having the Formula (I), Formula (II), Formula (III), Formula (III'), Formula (IV), Formula (IV'), Formula (IV'-a), and Formula (IV'-b) may be salts thereof.

Examples of the salt of the compound include a salt with inorganic acid, a salt with organic acid, and a salt with acidic amino acid.

Suitable examples of the salt with inorganic acid include salts with hydrofluoric acid, hydrochloric acid, hydrobromic acid, hydroiodic acid, nitric acid, sulfuric acid, sulfurous acid, phosphoric acid, phosphorous acid, carbonic acid, bicarbonate, and the like.

Suitable examples of the salt with organic acid include a salt with carboxylic acid (that is, an organic compound having one or more carboxy groups; specific examples thereof include formic acid, acetic acid, benzoic acid, trifluoroacetic acid, phthalic acid, fumaric acid, oxalic acid, tartaric acid, maleic acid, mandelic acid, citric acid, succinic acid, malic acid, and the like); a salt with sulfonic acid (that is, an organic compound having one or more sulfo groups; specific examples thereof include methanesulfonic acid, trifluoromethanesulfonic acid, benzenesulfonic acid, p-toluenesulfonic acid, and camphorsulfonic acid).

Suitable examples of the salt with acidic amino acid include salts with aspartic acid, glutamic acid, and the like.

In the above salts, pharmaceutically acceptable salts are preferable, and among them, salts of hydrochloric acid, fumaric acid, oxalic acid, citric acid, tartaric acid, mandelic acid, and sulfonic acid are preferable. More preferred example is mandelate or sulfonate. Among the "sulfonic acids", sulfonic acid having the following Formula (XI):

[Chem. 16]

$R^2SO_3H$ (XI)

wherein $R^2$ represents an optionally substituted hydrocarbon group is preferred.

Examples of a suitable "hydrocarbon group" in the "optionally substituted hydrocarbon group" represented by $R^2$ in the Formula (XI) include a $C_{1-6}$ alkyl group, a $C_{3-10}$ cycloalkyl group, a $C_{6-14}$ aryl group, and a $C_{7-16}$ aralkyl group, and among them, a $C_{1-6}$ alkyl group and a $C_{6-14}$ aryl group are preferred, and a $C_{6-14}$ aryl group is more preferred.

In Formula (XI), $R^2$ is preferably an optionally substituted $C_{6-14}$ aryl group; more preferably an optionally substituted phenyl group; further preferably a phenyl group optionally substituted with a $C_{1-6}$ alkyl group; and particularly preferably a phenyl group optionally substituted with methyl.

Specifically, the sulfonic acid of the Formula (XI) is preferably methanesulfonic acid, trifluoromethanesulfonic acid, benzenesulfonic acid, or p-toluenesulfonic acid, and more preferably p-toluenesulfonic acid.

The compounds of the Formula (III) and Formula (III') may be in a free form or in a salt form, but are more preferably in a free form.

The compounds having the Formula (IV), Formula (IV'), Formula (IV'-a), and Formula (IV'-b) may be in a free form or in a salt form, but are preferably in a salt form. The salt of the compound is preferably a salt with hydrochloric acid, oxalic acid, fumaric acid, mandelic acid, or sulfonic acid, more preferably a salt with hydrochloric acid, mandelic acid, or p-toluenesulfonic acid, and most preferably a salt with mandelic acid.

Preferred examples of the salt with mandelic acid may include compounds of the following Formula (VI) and Formula (VI').

[Chem. 7]

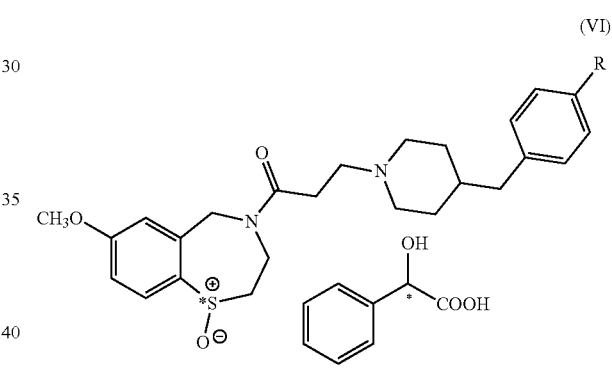

(VI)

wherein, * indicates the presence of optical isomers, and R represents a hydrogen atom or a hydroxyl group.

[Chem. 17]

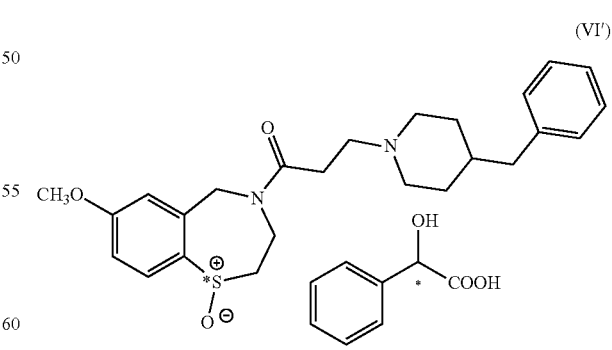

(VI')

wherein, * indicates the presence of optical isomers.

The mandelic acid to be a salt is preferably an optically active substance, and when the compounds having the Formula (IV) and Formula (IV') are the (R) form, (R)-mandelic acid is preferable, and when the compounds having the Formula (VII) and Formula (VII') are the (S) form, (S)-mandelic acid is preferable.

Preferred examples of the salt with sulfonic acid may include compounds of the following Formula (VII) and Formula (VII').

[Chem. 8]

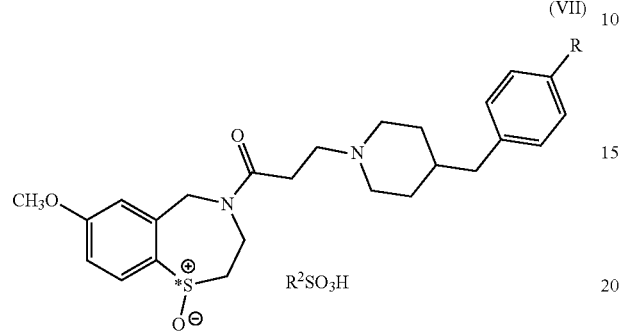

(VII)

wherein, $R^2$ represents an optionally substituted hydrocarbon group, * indicates the presence of optical isomers, and R represents a hydrogen atom or a hydroxyl group.

[Chem. 18]

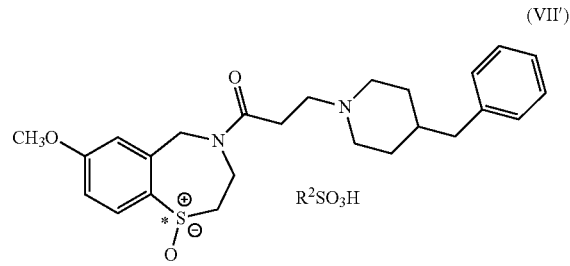

(VII')

wherein, * indicates the presence of optical isomers, R represents a hydrogen atom or a hydroxyl group, and $R^2$ represents an optionally substituted hydrocarbon group.

Preferred examples of the salt with hydrochloric acid may include compounds of the following Formula (VIII) and Formula (VIII').

[Chem. 9]

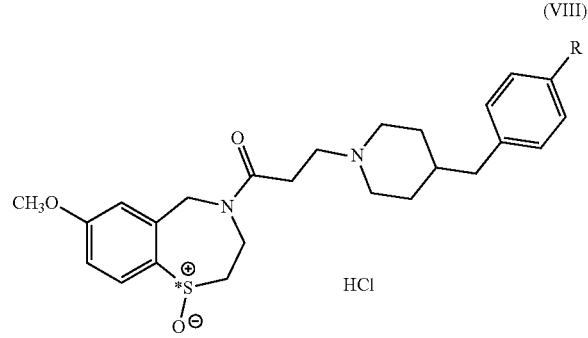

(VIII)

wherein, * indicates the presence of optical isomers, and R represents a hydrogen atom or a hydroxyl group.

[Chem. 19]

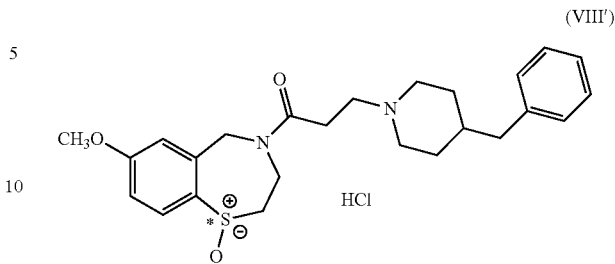

(VIII')

wherein, * indicates the presence of optical isomers, and R represents a hydrogen atom or a hydroxyl group.

Salts of the compounds having the Formula (II), Formula (IV'), Formula (IV'-a), and Formula (IV'-b), and compounds having the Formula (VI), Formula (VI'), Formula (VII), Formula (VII'), Formula (VIII), and Formula (VIII') which are compounds in a salt form may be prepared by producing the compounds as free forms by a reaction for oxidizing the corresponding sulfide compound, and then converting the compounds into compounds in a salt form. A person skilled in the art can appropriately convert a compound in a free form into any salt form exemplified above to prepare a compound in a salt form.

The compounds having the Formula (I), Formula (II), Formula (III), Formula (III'), Formula (IV), Formula (IV'), Formula (IV'-a), and Formula (IV'-b) or salts thereof, and the compounds in a salt form having the Formula (VI), Formula (VI'), Formula (VII), Formula (VII'), Formula (VIII), and Formula (VIII') may be solvates (for example, hydrate and ethanolate) or a non-solvates (for example, non-hydrate), respectively. The compounds in any form of solvates and non-solvates are included in compounds having the Formula (I), Formula (II), Formula (III), Formula (III'), Formula (IV), Formula (IV'), Formula (IV'-a), Formula (IV'-b), Formula (VI), Formula (VI'), Formula (VII), Formula (VII'), Formula (VIII), or Formula (VIII').

The compounds labeled with an isotope or the like in the above compounds are also included in the compounds having the Formula (I), Formula (II), Formula (III), Formula (III'), Formula (IV), Formula (IV'), Formula (IV'-a), Formula (IV'-b), Formula (VI), Formula (VI'), Formula (VII), Formula (VII'), Formula (VIII), or Formula (VIII').

A deuterium converted product obtained by converting $^1H$ into $^2H$ (D) in the above compound is also included in the compounds having the Formula (I), Formula (II), Formula (III), Formula (III'), Formula (IV), Formula (IV'), Formula (IV'-a), Formula (IV'-b), Formula (VI), Formula (VI'), Formula (VII), Formula (VII'), Formula (VIII), or Formula (VIII').

In the compounds of the Formula (V-a) and Formula (V-b) which are diol compounds, $R^1$ represents an optionally substituted $C_{2-6}$ alkyl group or benzyl.

Examples of the "optionally substituted $C_{2-6}$ alkyl group" include a $C_{2-6}$ alkyl group which may have a substituent selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group, (7) a $C_{6-14}$ aryloxy group (for example, phenoxy and naphthoxy),
(8) a $C_{7-16}$ aralkyloxy group (for example, benzyloxy),
(9) a 5 to 14 membered aromatic heterocyclic oxy group (for example, pyridyloxy),
(10) a 3 to 14 membered non-aromatic heterocyclic oxy group (for example, morpholinyloxy or piperidinyloxy),
(11) a $C_{1-6}$ alkyl-carbonyloxy group (for example, acetoxy or propanoyloxy),
(12) a $C_{6-14}$ aryl-carbonyloxy group (for example, benzoyloxy, 1-naphthoyloxy, or 2-naphthoyloxy),
(13) a $C_{1-6}$ alkoxy-carbonyloxy group (for example, methoxycarbonyloxy, ethoxycarbonyloxy, propoxycarbonyloxy, or butoxycarbonyloxy),
(14) a mono- or di-$C_{1-6}$ alkyl-carbamoyloxy group (for example, methylcarbamoyloxy, ethylcarbamoyloxy, dimethylcarbamoyloxy, or diethylcarbamoyloxy),
(15) a $C_{6-14}$ aryl-carbamoyloxy group (for example, phenylcarbamoyloxy or naphthylcarbamoyloxy),
(16) a 5 to 14 membered aromatic heterocyclic carbonyloxy group (for example, nicotinoyloxy),
(17) a 3 to 14 membered non-aromatic heterocyclic carbonyloxy group (for example, morpholinylcarbonyloxy or piperidinylcarbonyloxy),
(18) an optionally halogenated $C_{1-6}$ alkylsulfonyloxy group (for example, methylsulfonyloxy or trifluoromethylsulfonyloxy),
(19) a $C_{6-14}$ arylsulfonyloxy group optionally substituted with a $C_{1-6}$ alkyl group (for example, phenylsulfonyloxy or toluenesulfonyloxy),
(20) an optionally halogenated $C_{1-6}$ alkylthio group,
(21) a 5 to 14 membered aromatic heterocyclic group,
(22) a 3 to 14 membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5 to 14 membered aromatic heterocyclic carbonyl group,
(28) a 3 to 14 membered non-aromatic heterocyclic carbonyl group,
(29) a $C_{1-6}$ alkoxy-carbonyl group,
(30) a $C_{6-14}$ aryloxy-carbonyl group (for example, phenyloxycarbonyl, 1-naphthyloxycarbonyl, or 2-naphthyloxycarbonyl),
(31) a $C_{7-16}$ aralkyloxy-carbonyl group (for example, benzyloxycarbonyl or phenethyloxycarbonyl),
(32) a carbamoyl group,
(33) a thiocarbamoyl group,
(34) a mono- or di-$C_{1-6}$ alkyl-carbamoyl group,
(35) $C_{6-14}$ aryl-carbamoyl group (for example, phenylcarbamoyl),
(36) a 5 to 14 membered aromatic heterocyclic carbamoyl group (for example, pyridylcarbamoyl or thienylcarbamoyl),
(37) a 3 to 14 membered non-aromatic heterocyclic carbamoyl group (for example, morpholinylcarbamoyl or piperidinylcarbamoyl),
(38) an optionally halogenated $C_{1-6}$ alkylsulfonyl group,
(39) a $C_{6-14}$ arylsulfonyl group,
(40) a 5 to 14 membered aromatic heterocyclic sulfonyl group (for example, pyridylsulfonyl or thienylsulfonyl),
(41) an optionally halogenated $C_{1-6}$ alkylsulfinyl group,
(42) a $C_{6-14}$ arylsulfinyl group (for example, phenylsulfinyl, 1-naphthylsulfinyl, or 2-naphthylsulfinyl),
(43) a 5 to 14 membered aromatic heterocyclic sulfinyl group (for example, pyridylsulfinyl or thienylsulfinyl),
(44) an amino group,
(45) a mono- or di-$C_{1-6}$ alkylamino group (for example, methylamino, ethylamino, propylamino, isopropylamino, butylamino, dimethylamino, diethylamino, dipropylamino, dibutylamino, or N-ethyl-N-methylamino),
(46) a mono- or di-$C_{6-14}$ arylamino group (for example, phenylamino),
(47) a 5 to 14 membered aromatic heterocyclic amino group (for example, pyridylamino),
(48) a $C_{1-6}$ aralkylamino group (for example, benzylamino),
(49) a formylamino group,
(50) a $C_{1-6}$ alkyl-carbonylamino group (for example, acetylamino, propanoylamino, or butanoylamino),
(51) a ($C_{1-6}$ alkyl) ($C_{1-6}$ alkyl-carbonyl) amino group (for example, N-acetyl-N-methylamino),
(52) a $C_{6-14}$ aryl-carbonylamino group (for example, phenylcarbonylamino, or naphthylcarbonylamino),
(53) a $C_{1-6}$ alkoxy-carbonylamino group (for example, methoxycarbonylamino, ethoxycarbonylamino, propoxycarbonylamino, butoxycarbonylamino, or tert-butoxycarbonylamino),
(54) a $C_{4-16}$ aralkyloxy-carbonylamino group (for example, benzyloxycarbonylamino),
(55) a $C_{1-6}$ alkylsulfonylamino group (for example, methylsulfonylamino or ethylsulfonylamino),
(56) a $C_{6-14}$ arylsulfonylamino group optionally substituted with a $C_{1-6}$ alkyl group (for example, phenylsulfonylamino or toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the substituents in the "optionally substituted $C_{2-6}$ alkyl group" is, for example, 1 to 5, and preferably 1 to 3. When the number of substituents is two or more, the substituents may be the same as or different from each other.

$R^1$ is preferably an unsubstituted $C_{2-6}$ alkyl group and benzyl, more preferably ethyl, isopropyl, tert-butyl, and benzyl, and most preferably isopropyl.

The most preferred embodiment of the compound of the Formula (V-a) is (R,R)-diisopropyl tartarate.

The most preferred embodiment of the compound of the Formula (V-b) is (S,S)-diisopropyl tartarate.

Hereinafter, a method for producing an optically active substance of an optically active 1,4-benzothiazepine-1-oxide derivative (compound of the Formula (II)) or a salt thereof will be described in detail.

An optically active substance of the compound of the Formula (II) or a salt thereof can be produced by a production method of the following reaction formula.

Reaction Formula:

[Chem. 20]

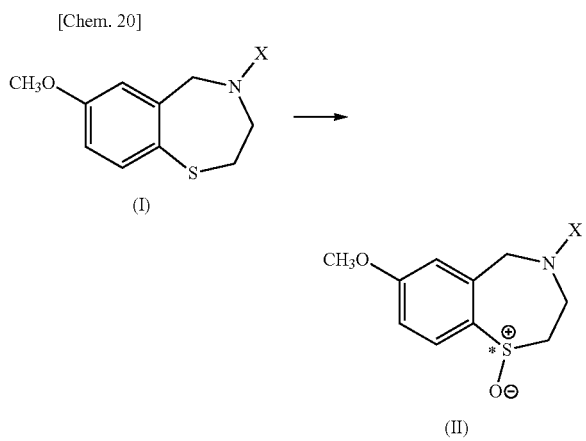

wherein * indicate the presence of optical isomers, and X represents a hydrogen atom or a substituent.

Reagents and conditions used in the production method will be described in detail below.

The above production method is a method for producing an optically active substance of the compound of the Formula (II) or a salt thereof by reacting the compound of the Formula (I) or a salt thereof with a reactant containing a titanium compound, a chiral diol compound, and water, and an oxidant in a solvent.

The chiral diol ligand may be a chiral diol compound having any structure as long as it functions as a reactant in the oxidation reaction of the present invention. Examples of the chiral diol include the following optically active compounds.

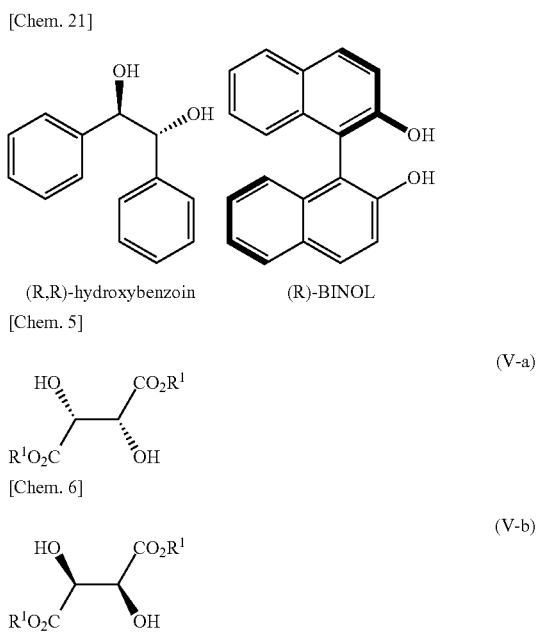

wherein $R^1$ represents an optionally substituted $C_{2-6}$ alkyl group or benzyl.

The chiral diol compound is preferably diol tartrate. The chiral diol is more preferably chiral diol tartrate having the above Formula (V-a) and Formula (V-b). More preferred examples include (R,R)-diethyl tartrate, (S,S)-diethyl tartrate, (R,R)-diisopropyl tartrate, (S,S)-diisopropyl tartrate, (R,R)-di-tert-butyl tartrate, (S,S)-di-tert-butyl tartrate, (R,R)-dibenzyl tartrate, and (S,S)-dibenzyl tartrate. Most preferably (R,R)-diisopropyl tartrate or (S,S)-diisopropyl tartrate, particularly (S,S)-diisopropyl tartrate.

As shown in Examples described later, when the (R,R)-diol tartrate compound is used, the (S) form of the compound (II) is excessively produced, and when the (S,S)-diol tartrate compound is used, the (R) form of the compound (II) is excessively produced.

The same applies to the production of the compounds having the Formula (IV), Formula (IV'), Formula (VI), Formula (VI'), Formula (VII), Formula (VII'), Formula (VIII), and Formula (VIII'). When a reactant containing a (R,R)-diol tartrate compound is used, a reaction product of the (S) form is excessively (preferentially) produced, and conversely, when a reactant containing a (S,S)-diol tartrate compound is used, a reaction product of the (R) form is excessively (preferentially) produced. Therefore, the production of the (S) form or the (R) form can be controlled by selecting an optical isomer of chiral diol tartarate.

The same applies to the control in the case of producing the compound of the Formula (IV'-a) which is a (R) form and the case of producing the compound of the Formula (IV'-b) which is a (S) form. In the former case, a (S,S)-diol tartrate compound such as a compound of the Formula (V-a) is preferably used.

In addition, in the latter case, a (R,R)-diol tartrate compound such as the compound of the Formula (V-b) is preferably used.

The reactant may be formed of an organometallic complex comprising a titanium compound and the chiral diol compound, and water.

As the organometallic complex, those obtained by isolating or purifying a chiral diol compound serving as a ligand and a titanium compound comprising titanium as a metal source, by employing known means (such as concentration, solvent extraction, fractional distillation, crystallization, recrystallization, and chromatography) can be used.

The organometallic complex may be prepared by adding "another complex comprising a titanium compound as a metal source" and "a chiral diol ligand" to a container. When an organometallic complex is prepared by adding the "other complexes comprising a titanium compound as a metal source" and the "chiral diol ligand" to a container, the "ligand" is added in a molar ratio of 1 to 100 times the theoretical amount necessary for constituting the organometallic complex. It is preferably used 1 to 5 times, and more preferably 1.01 to 2.02 times.

As the reactant, an isolated or purified organometallic complex may not be used. One aspect of the reactant is defined as a combination of a titanium compound, a chiral diol compound, and water, and when the combination is added to a reaction system containing a solvent, an action as a reactant is exerted, and the oxidation reaction of the present invention is achieved.

Even when an isolated or purified organometallic complex is not used, the preferred molar ratio of the titanium compound to the chiral diol ligand is as described above and is in the range of 1:1 to 1:100.

The ratio is more preferably 1:1 to 1:5, and still more preferably 1:1.01 to 1:2.02. As an example, an aspect in which a titanium compound and a chiral diol ligand are used in a molar ratio of 1:2 can be mentioned.

The titanium compound may be a titanium compound having any structure as long as it functions as a reactant in the oxidation reaction of the present invention. A preferred example of the titanium compound is titanium tetraisopropoxide.

As described above, the reactant contains water together with the titanium compound and the chiral diol compound. Water as the reactant can be used in any amount as long as the reaction of the present invention proceeds. A preferred amount of water utilized as the reactant is in the range of 0.1:1 to 10:1 in molar ratio with the titanium compound. A preferred molar ratio of water:the titanium compound is 0.3:1 to 3:1, and a more preferred molar ratio is 0.5:1 to 2:1. A more preferable molar ratio range is water:the titanium compound=1:1 to 1.3:1.

Examples of the oxidant include potassium hypochlorite, sodium hypochlorite, tert-butyl hypochlorite, potassium hypobromite, sodium hypobromite, potassium hypoiodite, sodium hypoiodite, tert-butyl hydroperoxide, cumene hydroperoxide, potassium peroxymonosulfate (oxone), methachlorobenzoic acid, and iodosylbenzene. An aqueous solution of tert-butyl hydroperoxide or cumene hydroperoxide is more preferable, and cumene hydroperoxide is most preferable.

The oxidant may be added to the reaction system by itself, or may be added to the reaction system in the form of a solution such as an aqueous solution.

Compounds as substrates for the reaction, that is, compounds having the Formula (I), Formula (III), and Formula (III'), or salts thereof can be synthesized by methods described in existing documents such as Patent Document 1, Patent Document 2, and Patent Document 3.

The reaction of the present invention shown above is performed in a solvent. Such a solvent is not particularly limited as long as it solubilizes a raw material compound, an organometallic complex, and an additive without inhibiting the reaction. Examples thereof include ethers such as diethyl ether, diisopropyl ether, tert-butyl methyl ether, diphenyl ether, tetrahydrofuran, 1,4-dioxane, methyltetrahydrofuran, 1,2-dimethoxyethane, 1,1-diethoxypropane, 1,1-dimethoxymethane, 2,2-dimethoxypropane, and anisole; alcohols such as ethanol, n-propanol, isopropyl alcohol, n-butanol, 2-butanol, tert-butyl alcohol, 3-methyl-1 butanol, 2-methyl-1 propanol, 1-pentanol, benzyl alcohol, 2-methoxyethanol, 2-ethoxyethanol, and ethylene glycol; aromatic hydrocarbons such as benzene, toluene, xylene, cumene, and chlorobenzene; saturated hydrocarbons such as hexane, heptane, pentane, cyclohexane, methylcyclohexane, isooctane, and petroleum ether; amides such as N,N-dimethylformamide, N,N-dimethylacetamide, formamide, hexamothylphosphoramide, N-methylpyrrolidone, and 1,3-dimethyl-2 imidazolidinone; halogenated hydrocarbons such as chloroform, dichloromethane, carbon tetrachloride, and 1,2-dichloroethane; nitriles such as acetonitrile and propionitrile; sulfoxides such as dimethyl sulfoxide; sulfones such as dimethylsulfone and sulfolane; ketones such as acetone, ethyl methyl ketone, methyl isopropyl ketone, and methyl butyl ketone; esters such as ethyl acetate, isopropyl acetate, n-propyl acetate, n-butyl acetate, isobutyl acetate, methyl acetate, and ethyl formate; nitromethane; and water. These solvents may be mixed and used in an appropriate ratio. Preferred examples of the solvent are toluene, chloroform, and ethyl acetate. Among them, toluene is particularly preferable.

The amount of the solvent to be used is appropriately determined depending on the solubility of a compound as a substrate for the reaction, that is, a compound having the Formula (I), Formula (III), and Formula (III'), or a salt thereof. For example, when toluene is used as the solvent, the reaction can be performed in a solvent that is 100 times or more by weight of the compound as a substrate or a salt thereof from a solvent-free state. It is preferable to use a solvent in an amount of about 2 to about 100 times by weight with respect to the compound which is usually a substrate or a salt thereof.

In one embodiment of the method of the present invention, a titanium compound (titanium tetraisopropoxide or the like) and a chiral diol ligand (for example, compound (V-a) or compound (V-b)) are added in a container containing a solvent prior to the oxidation reaction. Water used as a reactant is usually added after the addition as described later. However, the addition of water may be performed simultaneously or prior thereto.

The titanium compound (for example, titanium isopropoxide) is used in an amount of 0.01 to 10 mol, preferably 0.1 to 2 mol, and more preferably 0.5 to 1.5 mol, to the substrate (the compound having the Formula (I), Formula (III) and Formula (III') or salts thereof).

The reaction system can be constructed as follows.

A substrate (the compounds having the Formula (I), Formula (III), and Formula (III') or salts thereof) and water are added to a solution containing a titanium compound, a chiral diol ligand, and a solvent. The addition is desirably performed before the oxidant is added. A mixed liquid may be heated prior to the addition of the oxidant. The mixed liquid is heated to 40° C. to 70° C. or 50° C. to 55° C. Examples of the heating time are 0.1 to 3 hours and 0.5 to 1.2 hours.

Regardless of whether the heating operation is performed, when the temperature of the mixed liquid is higher than a predetermined reaction temperature, the mixed liquid is cooled to a desired reaction temperature. After cooling, an oxidant is added to start the oxidation reaction. The reaction temperature is −60° C. or higher and 20° C. or lower. The temperature is preferably −30° C. or higher and lower than 0° C. The temperature is more preferably −30° C. or higher and −10° C. or lower. The temperature is still more preferably −30° C. or higher and −20° C. or lower. The reaction time can be appropriately determined depending on the degree of progress of the reaction, but is usually 2 hours or more and 80 hours or less. The time is preferably 10 hours or more and 30 hours or less.

The use amount of the oxidant is 0.50 to 4.00 mol, and more preferably 0.95 to 2.02 mol, to the substrate (the compound having the Formula (I), Formula (III) and Formula (III') or salts thereof).

The reaction can be carried out under an atmosphere of air at normal pressure. In addition, air may be substituted with an inert gas by gas exchange, and the reaction may be performed in an inert gas atmosphere. Examples of the inert gas include nitrogen gas and argon gas. Preferably, argon gas is used.

When the substrate is a salt with an acidic substance, 1.0 to 1.3 mol of a base (for example, diisopropylethylamine, triethylamine, or pyridine) may be added to the substrate. However, the method of the present invention can generally achieve an asymmetric oxidation reaction with high conversion, high selectivity, and/or high optical purity (high enantioselectivity) without adding a base such as diisopropylethylamine.

The conversion according to the method of the invention ((total oxides/(residual substrate+total oxides)); %) is 50% or more, preferably 70% or more, and more preferably 90% or more.

The selectivity according to the method of the invention ((oxides of monoxides/total oxides); %) is 70% or more, preferably 90% or more, and more preferably 95% or more.

The optical purity (absolute value of enantiomeric excess) according to the method of the invention; % ee) is 50% or more, preferably 70% or more, and more preferably 90% or more.

Here, the total oxide means the sum of an oxide of a monoxide corresponding to a substrate that is a sulfide form and an oxide of a dioxide form. The amounts of the remaining substrate, the oxide of the monoxide form, and the oxide of the dioxide form are determined by separating them by HPLC and then measuring the area. When the enantiomeric excess is measured, the amounts of the oxides of the (R) form and (S) form monoxides can be separated and identified by HPLC by the method disclosed in Patent Document 1 and a method based thereon.

In examples described later, the enantiomeric excess is calculated so that the +value is given when the (R) form is preferentially produced and the −value is given when the (S) form is preferentially produced, and the results are displayed.

The reaction product (optically active compounds having the Formula (II), Formula (IV), Formula (IV'), Formula (IV'-a) and Formula (IV'-b) or salts thereof) obtained in the present reaction may be purified by known means (for example, a fractional recrystallization, a chiral column method, and a diastereomeric salt method).

In order to obtain a reaction product (optically active compounds having the Formula (II), Formula (IV'-a), and Formula (IV'-b), or salts thereof) having high optical purity, the reaction product can be purified by a fractional recrystallization method or a diastereomer salt method after the oxidation reaction. Among them, the crystallization of diastereomeric salts with optically active mandelic acid is preferred. The crystallization using (R)-mandelic acid is particularly suitable when the reaction product is the (R) form, and the crystallization using (S)-mandelic acid is particularly suitable when the reaction product is the (S) form. More specifically, (R)-mandelic acid (or (S)-mandelic acid) is added in a solvent after acid-base extraction of the reaction mixture after completion of the oxidation reaction, and thereby the mandelate of the optically active compound can be crystallized. Examples of the acid used for the acid-base extraction include citric acid and hydrochloric acid. Examples of the base include potassium carbonate. After the acid addition and the base addition are sequentially performed, the reaction product of the oxidation reaction is extracted by adding an organic solvent (for example, tetrahydrofuran, toluene, or mixtures thereof). The crystallization is preferably performed after solvent exchange after extraction. Examples of the solvent used at the time of the crystallization include ethyl acetate, isopropyl acetate, acetone, methyl ethyl ketone, methyl isobutyl ketone, cyclopentyl methyl ether, isopropanol, tetrahydrofuran, acetonitrile, ethanol, and toluene. Preferred examples of the solvent are ethyl acetate, acetone, toluene, tetrahydrofuran, and ethanol, and particularly preferred examples are acetone.

The (R)-mandelate of the compound of the Formula (IV'-a) can be prepared as stable crystals that do not deliquesce even in air, as in the examples described below.

Salts of the compounds having the Formula (II), Formula (IV), Formula (IV'), Formula (IV'-a), and Formula (IV'-b) can be formed by reacting a compound in a free form with an acid (p-toluenesulfonic acid, (R)-mandelic acid, and the like) in a solvent (for example, tetrahydrofuran, ethyl acetate, acetonitrile, or any mixture of two or more thereof.).

The hydrochloride of the compound can also be formed by salt exchange using a compound in a salt form other than the hydrochloride as a material. For example, a hydrochloride of a compound having the Formula (II), Formula (IV), Formula (IV'), Formula (IV'-a), and Formula (IV'-b) can be obtained by adding a solution containing HCl (for example, an ethyl hydrochloride solution, a hydrochloric acid methanol solution, or a hydrochloric acid methanol solution) to a solution or slurry containing a salt of the compound (fumarate, mandelate, p-toluenesulfonate, methanesulfonate, or the like). Preferred examples of the salt of the compound to be a material are (R)-mandelate. The solution or slurry containing the salt of the compound preferably contains tetrahydrofuran, ethyl acetate, acetonitrile, or any mixture of two or more thereof as a solvent. More preferable is ethyl acetate, a mixture of ethyl acetate and acetonitrile, or a mixture of tetrahydrofuran and acetonitrile, and particularly preferable is a mixture of tetrahydrofuran and acetonitrile. A preferred example of a solution containing HCl is an ethyl acetate hydrochloride solution (HCl/EtOAc). The salt of the compound to be a material and HCl in the solution containing HCl may be used in any ratio, but are preferably used in an equivalent ratio in the range of 1:1.1 to 1:1.5. The addition can be performed under any temperature environment, but is preferably performed under a room temperature environment. The hydrochloride of the compound can be precipitated by adding and mixing for a certain period of time. After mixing at room temperature for a certain period of time, cooling (for example, 0° C.) may be performed.

The precipitated precipitate can be isolated as crystals of the hydrochloride of the compound by washing with a cold solvent (for example, ethyl acetate, tetrahydrofuran, or acetone) and then drying under reduced pressure.

EXAMPLES

The present invention will be further described in detail by the following test examples and examples, but these examples are merely examples and do not limit the present invention, and may be changed without departing from the scope of the present invention.

"Room temperature" in the following Test Examples and Examples usually indicates about 10° C. to about 35° C.

Chemical yield is expressed as isolation yield (mol/mol %) or yield obtained by high performance liquid chromatography.

The optical purity (asymmetric yield) of the optically active substance was evaluated by enantiomeric excess (% e.e.). The enantiomeric excess was determined by the following formula.

Enantiomeric excess(% e.e.)=100×[(R)−(S)]/[(R)+(S)](in the formula, (R) and (S) each represent an area of each enantiomer in high performance liquid chromatography.)

The amount of solvent used in chromatography is expressed in % by volume. The amounts of other substances used are expressed in % by weight.

In the analysis result of a proton NMR spectrum, data is not described for those in which peak values cannot be checked in a broad range, such as OH and NH protons.

Abbreviations used in other texts have the following meanings.

s: singlet
d: doublet
t: triplet
q: quartet
m: multiplet br: broad
J: coupling constant
Hz: Hertz
CDCl$_3$: heavy chloroform
DMSO-d$_6$: heavy dimethyl sulfoxide
CD$_3$OD: heavy methanol
$^1$H-NMR: proton nuclear magnetic resonance
$^{13}$C-NMR: $^{13}$C nuclear magnetic resonance In the following examples, nuclear magnetic resonance spectra (NMR) were measured under the following conditions.

$^1$H nuclear magnetic resonance spectrum ($^1$H NMR): BRUKER AVANCE 500 (500 MHz) manufactured by Bruker Corporation, internal standard substance: Tetramethylsilane $^{13}$C nuclear magnetic resonance spectrum ($^{13}$C NMR): BRUKER AVANCE 500 (125 MHz) manufactured by Bruker Corporation, internal standard substance: CDCl$_3$ In the following test examples, dynamic vapor sorption (DVS) were tested with DVS Adventure 1 from Surface Measurement Systems.

Example 1

Synthesis of 4-[3-(4-benzylpiperidin-1-yl)propionyl]-7-methoxy-2,3,4,5-tetrahydro-1,4-benzothiazepine-1-oxide (2)

[Chem. 22]

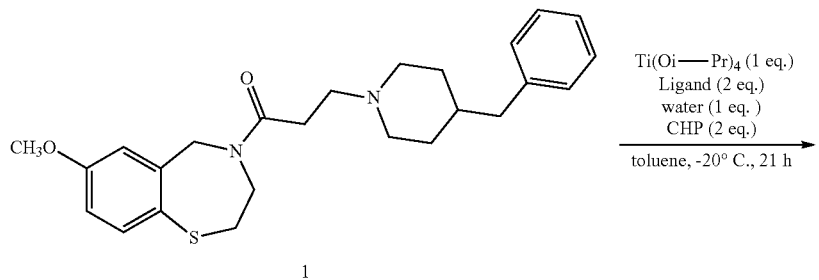

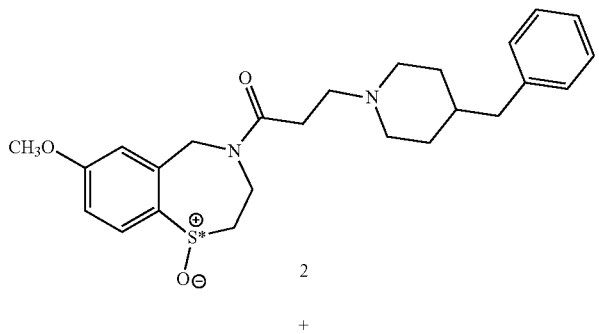

+

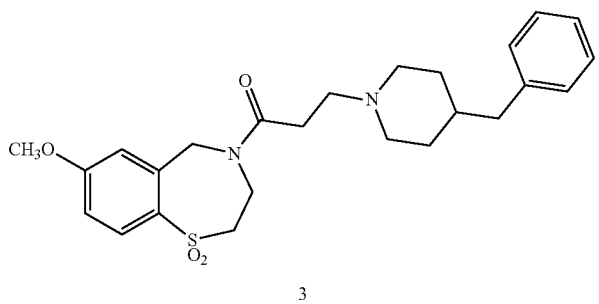

A solvent (toluene or dichloromethane) (1.5 mL), (R,R)-diethyl tartrate (0.0514 mL) and titanium tetraisopropoxide (0.0444 mL) were added to a test tube, and the mixture was stirred at room temperature for 3 minutes or more. Water (0.0027 mL) was then added, and the mixture was stirred at room temperature for 3 minutes or more. Subsequently, 4-[3-(4-benzylpiperidin-1-yl)propionyl]-7-methoxy-2,3,4,5-tetrahydro-1,4-benzothiazepine (1) (0.0637 g) or fumarate (0.0853 g) of (1) was added thereto, and the mixture was stirred at room temperature for 20 minutes. The reaction mixture was cooled, cumene hydroperoxide (2 equivalents based on (1)) was added at −20° C., and the mixture was stirred at −20° C. for 21 hours. Based on the area obtained by HPLC, the conversion to (2), the selectivity, and the enantiomeric excess of ((R)-2) were calculated.

Conversion=((2)+(3))/((1)+(2)+(3))

Selectivity=((2))/((2)+(3))

Here, in the above Formula 2, (2) represents a total value of (R)-2 and (S)-2.

The enantiomeric excess (% e.e.) of ((R)-2) was calculated by 100×[((R)-2)-((S)-2)]/[(R)-2)+((S)-2)] as described above.

The results are shown in Table 1. A negative enantiomeric excess value in the table indicates that ((S)-2) is a main product.

High performance liquid chromatography analysis conditions (Area percentage, optical purity)

Column: CHIRALPAK IC (manufactured by Daicel Corporation), 4.6*250 mm

UV detection wavelength: 245 nm

Mobile phase: acetonitrile/methanol/diethylamine for high performance liquid chromatography=900/100/1

Flow rate: 1.0 mL/min

Column temperature: 40° C.

Retention time: 5.0 min. (1), 5.6 min. (3), 9.8 min. ((R)-2), 12.5 min. ((S)-2)

It has been checked that ((R)-2) is the same compound as the first optical isomer component of Patent Document 1, and ((S)-2) is the same compound as the second optical isomer component of Patent Document 1.

TABLE 1

| entry | starting material | solvent | ratio conversion | selectivity | % ee of (R)-2 |
|---|---|---|---|---|---|
| 1 | 1·fumarate | CH$_2$Cl$_2$ | 0.35 | 0.98 | −41.1 |
| 2 | 1 | CH$_2$Cl$_2$ | 0.64 | 0.90 | −55.7 |
| 3 | 1·fumarate | toluene | 0.44 | 0.97 | −66.9 |
| 4 | 1 | toluene | 0.72 | 0.91 | −68.2 |

Regardless of whether a substrate (1) is a free form or fumarate, a monoxide compound (2) was produced with high selectivity.

In the present example using (R,R)-diethyl tartarate as a chiral diol compound, ((S)-2), which is a monoxide compound in a (S) form, was produced as a main product.

Asymmetric synthesis was able to be performed using any solvent of toluene and dichloromethane, but toluene provided higher optical purity under the conditions of the present example.

Example 2

Synthesis of 4-[3-(4-benzylpiperidin-1-yl)propionyl]-7-methoxy-2,3,4,5-tetrahydro-1,4-benzothiazepine-1-oxide (2)

[Chem. 23]

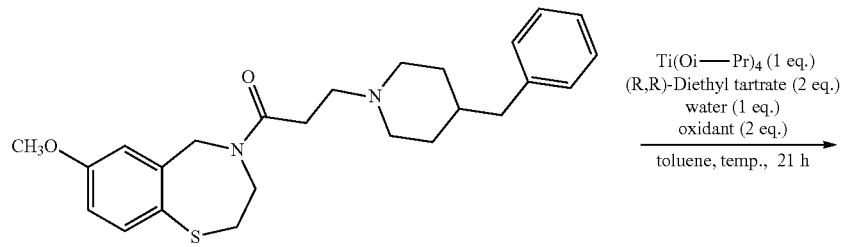

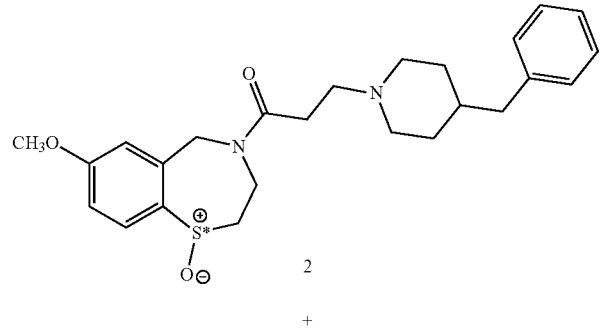

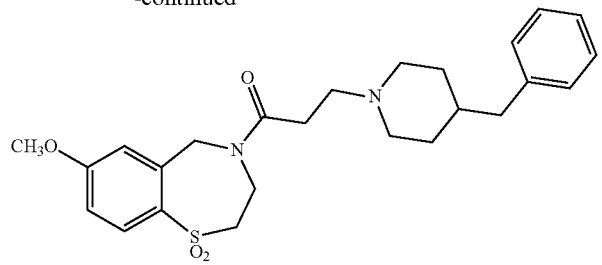

3

Toluene (1.5 mL), (R,R)-diethyl tartrate (0.0514 mL) and titanium tetraisopropoxide (0.0444 mL) were added to a test tube, and the mixture was stirred at room temperature for 3 minutes or more. Water (0.0027 mL) was then added, and the mixture was stirred at room temperature for 3 minutes or more. Subsequently, 4-[3-(4-benzylpiperidin-1-yl)propionyl]-7-methoxy-2,3,4,5-tetrahydro-1,4-benzothiazepine (1) (0.0637 g) was added thereto, and the mixture was stirred at room temperature for 20 minutes. After the reaction mixture was adjusted to a prescribed temperature, an oxidant (2 equivalents with respect to (1)) was added thereto, and the mixture was stirred at the same temperature for 21 hours. The conversion to (2) and the enantiomeric excess of ((R)-2) were calculated by HPLC.

The results are shown in Table 2. A negative enantiomeric excess value in the table indicates that ((S)-2) is a main product.

High performance liquid chromatography analytical conditions (Area percentage, optical purity) were the same as those in Example 1.

TABLE 2

| entry | Oxidant | temp. | conversion | selectivity | % ee of (R)-2 |
|---|---|---|---|---|---|
| 1 | 70% t-butyl hydroperoxide aqueous solution | −20° C. | 0.50 | 0.93 | −70.9 |
| 2 | 30% hydrogen peroxide aqueous solution | −20° C. | 1.00 | 0.01 | nd |
| 3 | 70% t-butyl hydroperoxide aqueous solution | 0° C. | 0.59 | 0.78 | −39.3 |
| 4 | 70% t-butyl hydroperoxide aqueous solution | rt | 0.88 | 0.34 | −34.5 |

When a 70% t-butyl hydroperoxide aqueous solution was used as an oxidant, an asymmetric synthesis reaction having ((S)-2) as a main product was checked. In a case where the reaction temperature was −20° C., higher optical purity was observed than in a case of 0° C. or room temperature.

When a 30% hydrogen peroxide aqueous solution was used as an oxidant, the obtained oxide was almost entirely a dioxide compound (3).

Example 3

Synthesis of 4-[3-(4-benzylpiperidin-1-yl)propionyl]-7-methoxy-2,3,4,5-tetrahydro-1,4-benzothiazepine-1-oxide (2)

[Chem. 24]

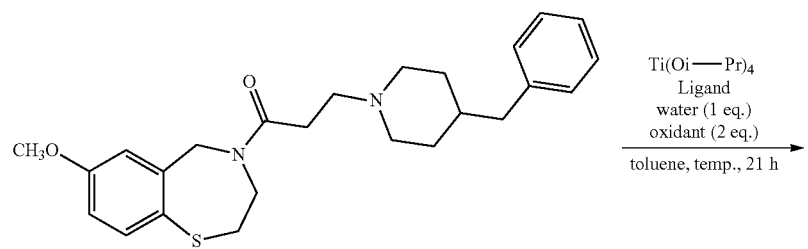

1

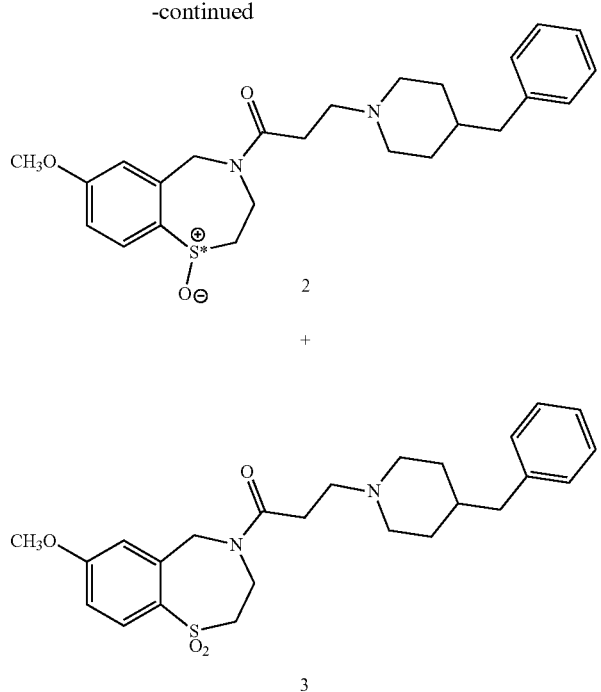

Toluene (1.5 mL), a chiral diol compound (ligand) (2 equivalents based on Ti(Oi-Pr)$_4$), and titanium tetraisopropoxide (specified amount based on (1)) were added to a 20 mL Schlenk tube under an argon atmosphere, and the mixture was stirred at room temperature for 3 minutes or more. Water (0.0027 mL) was then added, and the mixture was stirred at room temperature for 3 minutes or more. Subsequently, 4-[3-(4-benzylpiperidin-1-yl)propionyl]-7-methoxy-2,3,4,5-tetrahydro-1,4-benzothiazepine (1) (0.0637 g) was added thereto, and the mixture was stirred at room temperature for 20 minutes. The reaction mixture was cooled as necessary, cumene hydroperoxide or the 70% t-butyl hydroperoxide aqueous solution as an oxidant (2 equivalents based on (1)) was then added at a specified temperature, and the mixture was stirred at the same temperature for 21 hours. The conversion to (2) and the enantiomeric excess of ((R)-2) were calculated by HPLC.

The results are shown in Table 3. A negative enantiomeric excess value in the table indicates that ((S)-2) is a main product. In addition, the structural formulas of (R,R)-diethyl tartrate, (S,S)-dimethyl tartrate, (S,S)-diisopropyl tartrate, (R,R)-dit-butyl tartrate, (R,R)-dibenzyl tartrate, (R,R)-hydroxybenzoin, (R)-binaphthol, and (S)-dibromobinaphthol, which are the chiral diol compounds (ligands) used, are also shown below.

High performance liquid chromatography analytical conditions (Area percentage, optical purity) were the same as those in Example 1.

TABLE 3

| entry | Ti complex/Ligand | Oxidant | temp. | ratio conversion | selectivity | % ee of (R)-2 |
|---|---|---|---|---|---|---|
| 1 | Ti(Oi-Pr)$_4$(1 eq.)/(R,R)-DET (2 eq.) | cumene hydroperoxide | −20° C. | 0.86 | 0.89 | −69.3 |
| 2 | Ti(Oi-Pr)$_4$(1 eq.)/(S,S)-DMT (2 eq.) | cumene hydroperoxide | −20° C. | 0.05 | 1.00 | −3.7 |
| 3 | Ti(Oi-Pr)$_4$(1 eq.)/(S,S)-DIPT (2 eq.) | cumene hydroperoxide | −20° C. | 0.91 | 0.84 | 74.6 |
| 4 | Ti(Oi-Pr)$_4$(1 eq.)/(R,R)-DTBT (2 eq.) | cumene hydroperoxide | −20° C. | 0.67 | 0.79 | −12.7 |
| 5 | Ti(Oi-Pr)$_4$(1 eq.)/(R,R)-DBnT (2 eq.) | cumene hydroperoxide | −20° C. | 0.74 | 0.94 | −62.4 |
| 6 | Ti(Oi-Pr)$_4$(0.2 eq.)/(R,R)-hydroxybenzoin (0.4 eq.) | cumene hydroperoxide | −20° C. | 0.03 | 1.00 | 19.2 |
| 7 | Ti(Oi-Pr)$_4$(0.2 eq.)/(R)-BINOL (0.4 eq.) | cumene hydroperoxide | −20° C. | 0.02 | 1.00 | 20.0 |
| 8 | Ti(Oi-Pr)$_4$(0.2 eq.)/(S)-Br-BINOL (0.4 eq.) | cumene hydroperoxide | −20° C. | 0.12 | 0.88 | 2.0 |
| 9 | Ti(Oi-Pr)$_4$(0.2 eq.)/(R,R)-hydroxybenzoin (0.4 eq.) | 70% t-butyl hydroperoxide aqueous solution | rt | 0.46 | 0.92 | 0.8 |
| 10 | Ti(Oi-Pr)$_4$(0.2 eq.)/(R)-BINOL (0.4 eq.) | 70% t-butyl hydroperoxide aqueous solution | rt | 0.35 | 0.93 | 29.1 |

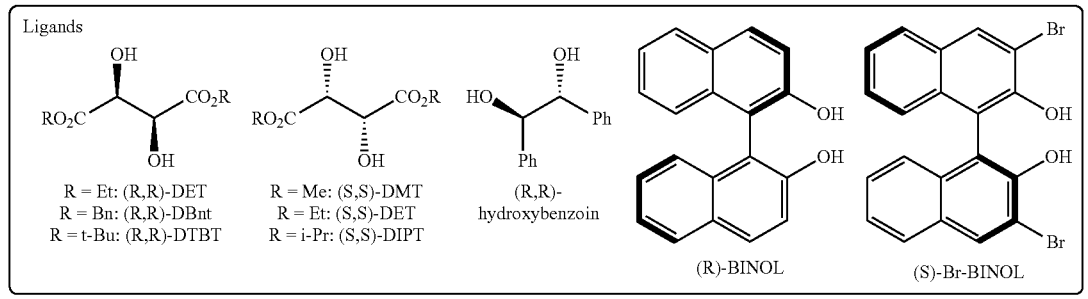

Under the above conditions, when (S,S)-dimethyl tartrate, (R,R)-hydroxybenzoin, (R)-binaphthol, or (S)-dibromobinaphthol was used as the chiral diol compound (ligand), a sufficient oxidation reaction to the monoxide compound was not observed.

On the other hand, when (R,R)-diethyl tartrate or (R,R)-dibenzyl tartrate was used as the chiral diol compound (ligand), an asymmetric synthesis reaction having ((S)-2) as a main product was achieved, and when (S,S)-diisopropyl tartrate was used, an asymmetric synthesis reaction having ((R)-2) as a main product was achieved. Under these conditions, both the conversion and the selectivity showed sufficiently high values.

Example 4

Synthesis of (R)-4-[3-(4-benzylpiperidin-1-yl)propionyl]-7-methoxy-2,3,4,5-tetrahydro-1,4-benzothiazepine-1-oxide ((R)-2)

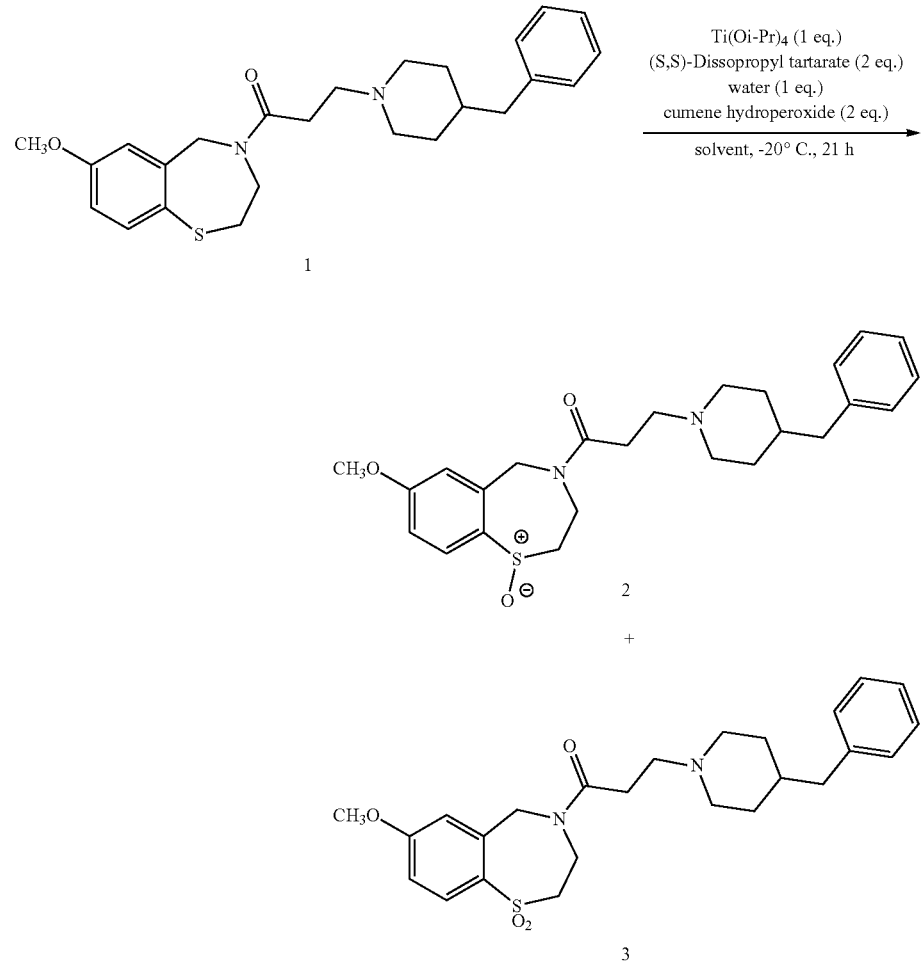

A solvent (1.5 mL), (S,S)-diisopropyl tartrate (0.1361 mL), and titanium tetraisopropoxide (0.0962 mL) were added to a 20 mL Schlenk tube under an argon atmosphere, and the mixture was stirred at room temperature for 3 minutes or more. Water (0.0059 mL) was then added, and the mixture was stirred at room temperature for 3 minutes or more. Subsequently, 4-[3-(4-benzylpiperidin-1-yl)propionyl]-7-methoxy-2,3,4,5-tetrahydro-1,4-benzothiazepine (1) (0.1380 g) was added thereto, and the mixture was stirred at room temperature for 20 minutes. The reaction mixture was cooled, cumene hydroperoxide (0.1189 mL) was then added thereto at −20° C., and the mixture was stirred at the same temperature for 21 hours. The conversion to (2) and the enantiomeric excess of ((R)-2) were calculated by HPLC.

As the solvent, any one of toluene, dichloromethane, chloroform, acetonitrile, tetrahydrofuran, ethyl acetate, methanol, ethanol, and isopropyl alcohol was used.

The results are shown in Table 4.

High performance liquid chromatography analytical conditions (Area percentage, optical purity) were the same as those in Example 1.

TABLE 4

| entry | solvent | ratio | | % ee of (R)-2 |
|---|---|---|---|---|
| | | conversion | selectivity | |
| 1 | toluene | 0.98 | 0.73 | 79.1 |
| 2 | CH$_2$Cl$_2$ | 0.86 | 0.84 | 37.8 |
| 3 | CHCl$_3$ | 0.95 | 0.87 | 53.3 |
| 4 | MeCN | 0.88 | 0.74 | 33.6 |
| 5 | THF | 0.92 | 0.49 | 24.9 |
| 6 | EtOAc | 0.97 | 0.50 | 50.0 |
| 7 | MeOH | 0.12 | 1.00 | 17.1 |
| 8 | EtOH | 0.67 | 0.94 | 30.9 |
| 9 | IPA | 0.97 | 0.73 | 24.4 |

When a solvent other than methanol was used, a sufficiently high conversion was obtained. In particular, when toluene, chloroform, and ethyl acetate were used, high values were obtained in terms of selectivity and optical purity, and the optical isomer of ((R)-2) was produced in good yield.

Example 5

Synthesis of (R)-4-[3-(4-benzylpiperidin-1-yl)propionyl]-7-methoxy-2,3,4,5-tetrahydro-1,4-benzothiazepine-1-oxide ((R)-2)

[Chem. 27]

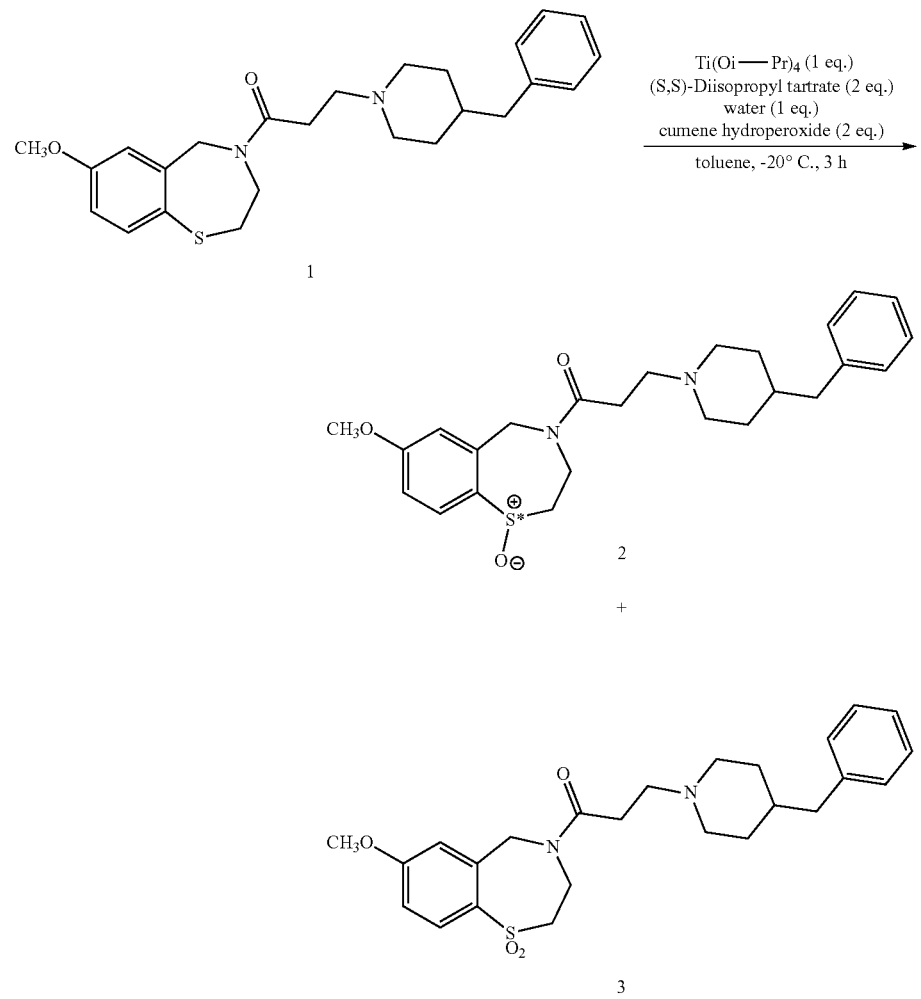

Toluene (1.5 mL), (S,S)-diisopropyl tartrate (0.1361 mL), and titanium tetraisopropoxide (0.0962 mL) were added to a 20 mL Schlenk tube under an argon atmosphere, and the mixture was stirred at room temperature for 3 minutes. Water (0.0059 mL) was then added, and the mixture was stirred at room temperature for 3 minutes. Subsequently, 4-[3-(4-benzylpiperidin-1-yl)propionyl]-7-methoxy-2,3,4,5-tetrahydro-1,4-benzothiazepine (1) (0.1380 g) was added thereto, and then the temperature was raised to 50° C., and the mixture was stirred for 2 hours. The reaction mixture was cooled, cumene hydroperoxide (0.1189 mL) was then added thereto at −20° C., and the mixture was stirred at the same temperature for 3 hours.

The results were: HPLC conversion: 97%, selectivity of (2)/(3): 93%, enantiomeric excess: 91.2% ee. In the present example in which (S,S)-diisopropyl tartrate was used as a chiral diol compound, cumene hydroperoxide was used as an oxidant, and toluene was used as a solvent, a reaction having extremely high conversion and selectivity and excellent optical purity was achieved, and an optical isomer of ((R)-2) was obtained with high yield.

Example 6

Synthesis of (R)-4-[3-(4-benzylpiperidin-1-yl)propionyl]-7-methoxy-2,3,4,5-tetrahydro-1,4-benzothiazepine-1-oxide ((R)-2)

[Chem. 28]

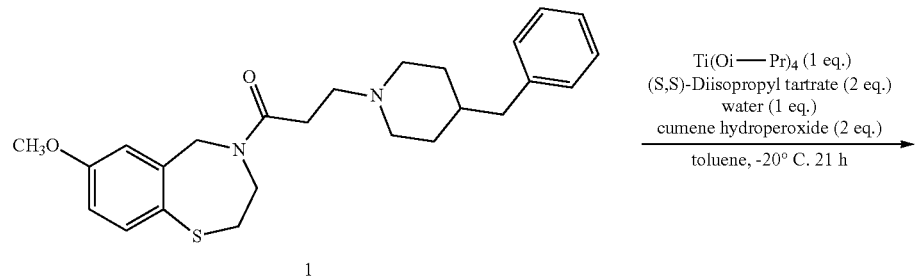

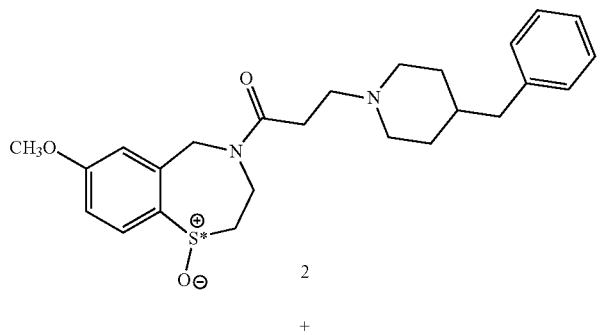

+

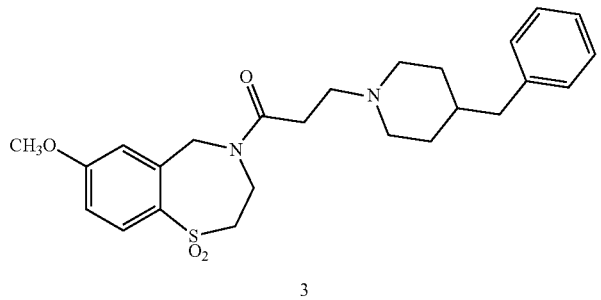

Toluene (1.5 mL), (S,S)-diisopropyl tartrate (0.1361 mL), and titanium tetraisopropoxide (0.0962 mL) were added to a 20 mL Schlenk tube under an argon atmosphere, and the mixture was stirred at room temperature for 3 minutes. Water (0.0059 mL) was then added, and the mixture was stirred at room temperature for 3 minutes. Subsequently, 4-[3-(4-benzylpiperidin-1-yl)propionyl]-7-methoxy-2,3,4,5-tetrahydro-1,4-benzothiazepine (1) (0.1380 g) was added thereto, and then the temperature was raised to 50° C., and the mixture was stirred for 2 hours. The reaction mixture was cooled, cumene hydroperoxide (0.1189 mL) was then added thereto at −20° C., and the mixture was stirred at the same temperature for 21 hours.

The results were: HPLC conversion: 100%, selectivity of (2)/(3): 66%, enantiomeric excess: 96.1% ee.

In comparison with the results of Example 5, it has become clear that 3 hours is sufficient as the reaction time under the conditions of these examples.

Example 7

Synthesis of (R)-4-[3-(4-benzylpiperidin-1-yl)propionyl]-7-methoxy-2,3,4,5-tetrahydro-1,4-benzothiazepine-1-oxide ((R)-2)

Toluene (1.5 mL), (S,S)-diisopropyl tartrate (0.1361 mL), and 4-[3-(4-benzylpiperidin-1-yl)propionyl]-7-methoxy-2,3,4,5-tetrahydro-1,4-benzothiazepine (1) (0.1380 g) were added to a 20 mL Schlenk tube under an argon atmosphere, and the mixture was stirred at room temperature for 3 minutes. Subsequently, titanium tetraisopropoxide (0.0962 mL) was added, and the mixture was stirred at room temperature for 3 minutes. Water (0.0059 mL) was added thereto, then the temperature was raised to 50° C., and the mixture was stirred for 2 hours. The reaction mixture was cooled, cumene hydroperoxide (0.1189 mL) was then added thereto at −20° C., and the mixture was stirred at the same temperature for 3 hours.

The results were: HPLC conversion: 96%, selectivity of (2)/(3): 95%, enantiomeric excess: 92.2% ee.

The order of addition of the substrate and the titanium compound was different between Example 5 and the present example, but in all examples, both the conversion and the selectivity were extremely high, and a reaction excellent in the optical purity was achieved, so that an optical isomer of ((R)-2) was obtained with high yield.

[Chem. 27]

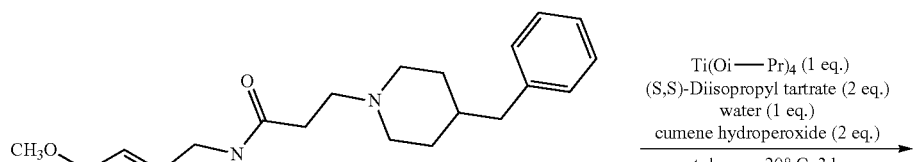

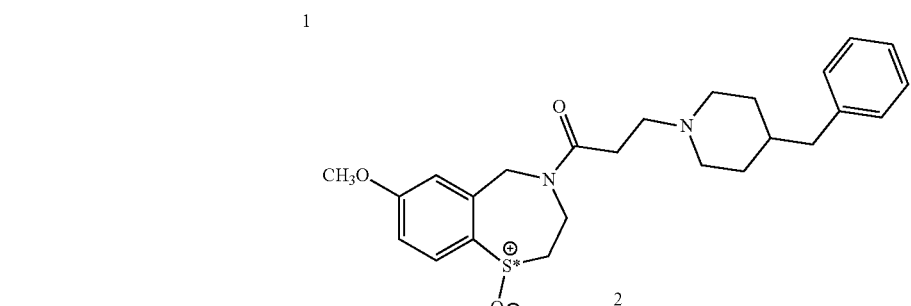

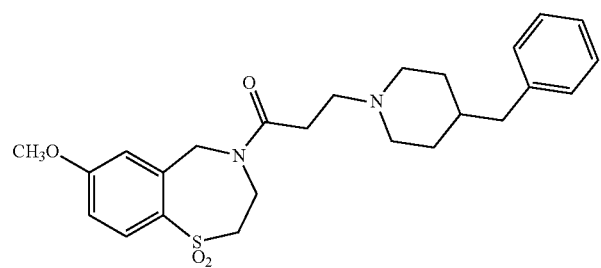

Example 8

Synthesis of (R)-4-[3-(4-benzylpiperidin-1-yl)propionyl]-7-methoxy-2,3,4,5-tetrahydro-1,4-benzothiazepine-1-oxide ((R)-2)

[Chem. 27]

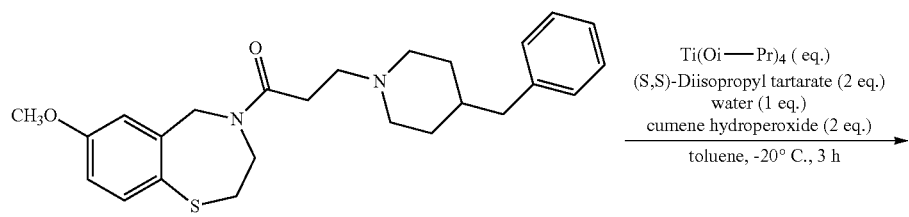

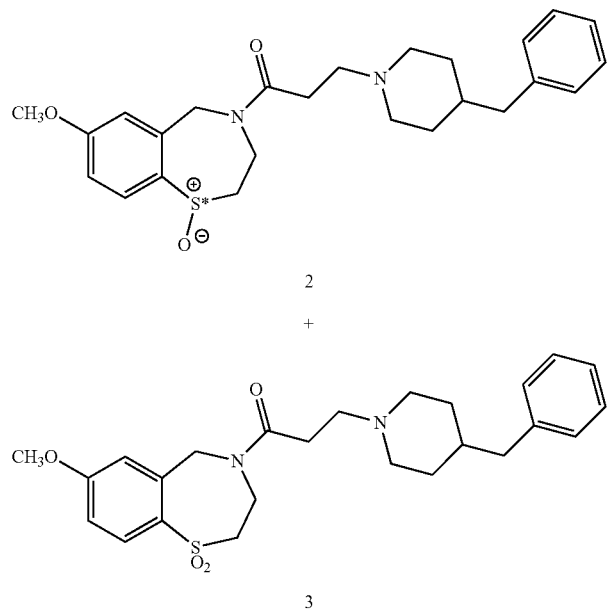

Toluene (1.5 mL), (S,S)-diisopropyl tartrate (0.1361 mL), and titanium tetraisopropoxide (0.0962 mL) were added to a 20 mL Schlenk tube under an argon atmosphere, and the mixture was stirred at room temperature for 3 minutes. Subsequently, 4-[3-(4-benzylpiperidin-1-yl)propionyl]-7-methoxy-2,3,4,5-tetrahydro-1,4-benzothiazepine (1) (0.1380 g) was added thereto, and the mixture was stirred at room temperature for 3 minutes. Water (0.0059 mL) was added thereto, then the temperature was raised to 50° C., and the mixture was stirred for 2 hours. The reaction mixture was cooled, cumene hydroperoxide (0.1189 mL) was then added thereto at −20° C., and the mixture was stirred at the same temperature for 3 hours.

The results were: HPLC conversion: 95%, selectivity of (2)/(3): 95%, enantiomeric excess: 91.8% ee.

The order of addition of the substrate and water was different between Example 5 and the present example, but in all examples, both the conversion and the selectivity were extremely high, and a reaction excellent in the optical purity was achieved, so that an optical isomer of ((R)-2) was obtained with high yield.

Example 9

Synthesis of (R)-4-[3-(4-benzylpiperidin-1-yl)propionyl]-7-methoxy-2,3,4,5-tetrahydro-1,4-benzothiazepine-1-oxide ((R)-2)

[Chem. 29]

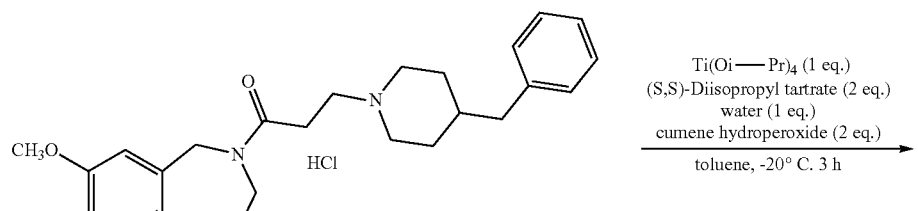

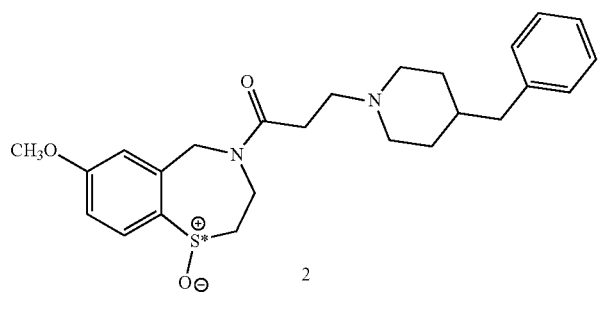

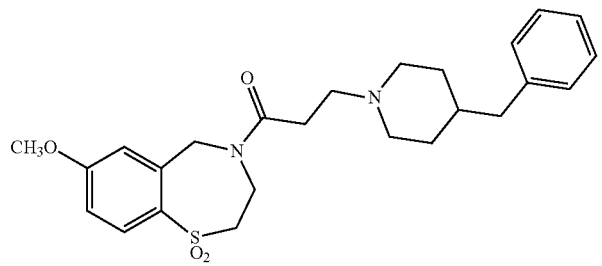

Toluene (1.5 mL), (S,S)-diisopropyl tartrate (0.1361 mL), and titanium tetraisopropoxide (0.0962 mL) were added to a 20 mL Schlenk tube under an argon atmosphere, and the mixture was stirred at room temperature for 3 minutes. Subsequently, 4-[3-(4-benzylpiperidin-1-yl)propionyl]-7-methoxy-2,3,4,5-tetrahydro-1,4-benzothiazepine (1) hydrochloride (0.1500 g) was added thereto, and the mixture was stirred at room temperature for 3 minutes. Water (0.0059 mL) was added thereto, then the temperature was raised to 50° C., and the mixture was stirred for 2 hours. The reaction mixture was cooled, cumene hydroperoxide (0.1189 mL) was then added thereto at −20° C., and the mixture was stirred at the same temperature for 3 hours.

The results were: HPLC conversion: 70%, selectivity of (2)/(3): 96%, enantiomeric excess: 57.0% ee.

Even when the salt of (1) was used as a substrate, sufficient conversion and selectivity were obtained, it was possible to produce the optically active monoxide compound of ((R)-2) with high optical purity.

Example 10

Synthesis of (R)-4-[3-(4-benzylpiperidin-1-yl)propionyl]-7-methoxy-2,3,4,5-tetrahydro-1,4-benzothiazepine-1-oxide ((R)-2)

[Chem. 30]

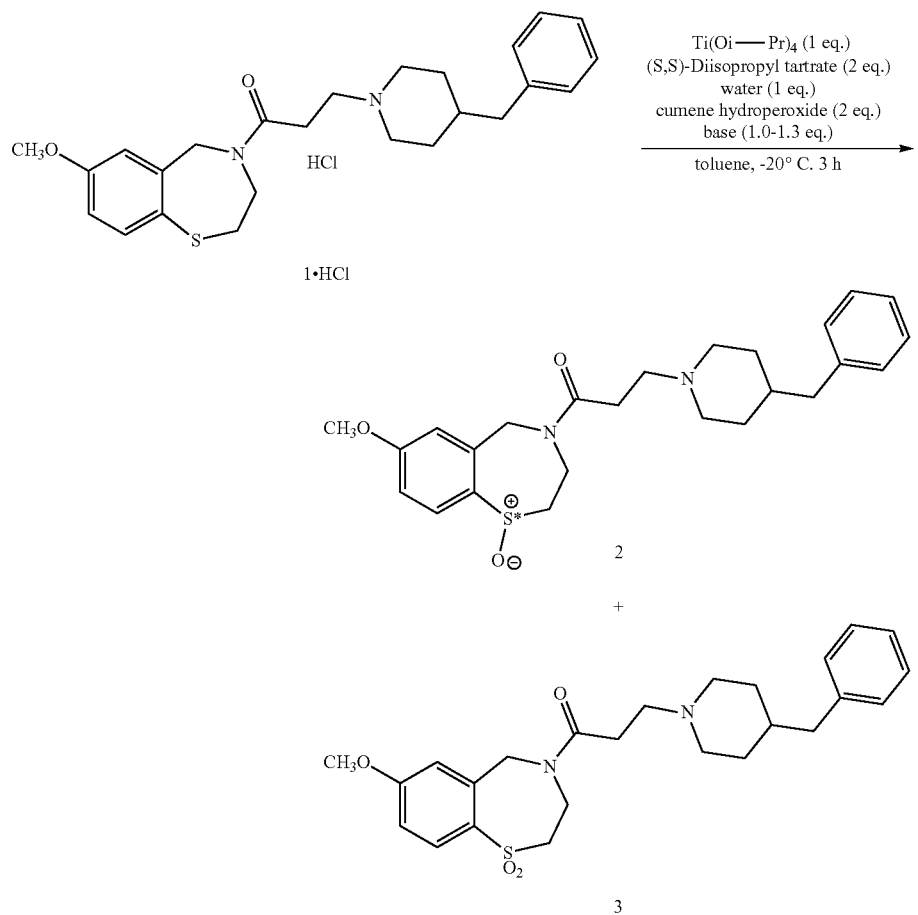

Toluene (1.5 mL), (S,S)-diisopropyl tartrate (0.1361 mL), and titanium tetraisopropoxide (0.0962 mL) were added to a 20 mL Schlenk tube under an argon atmosphere, and the mixture was stirred at room temperature for 3 minutes. Subsequently, 4-[3-(4-benzylpiperidin-1-yl)propionyl]-7-methoxy-2,3,4,5-tetrahydro-1,4-benzothiazepine (1) hydrochloride (0.150 g) and a base (1.0 to 1.3 equivalents to 1) were added and stirred at room temperature for 3 minutes. Water (0.0059 mL) was added thereto, then the temperature was raised to 50° C., and the mixture was stirred for 2 hours. The reaction mixture was cooled, cumene hydroperoxide (0.1189 mL) was then added thereto at −20° C., and the mixture was stirred at the same temperature for 3 hours.

The conversion to (2) and the enantiomeric excess of (R)-2 were calculated by HPLC.

The results are shown in Table 5.

TABLE 5

| entry | base | ratio conversion | ratio selectivity | % ee of (R)-2 |
|---|---|---|---|---|
| 1 | Diisoproplethylamine (1.0 eq.) | 0.88 | 0.95 | 88.0 |
| 2 | Triethylamine (1.0 eq.) | 0.86 | 0.96 | 87.0 |
| 3 | pyridine (1.0 eq.) | 0.60 | 0.96 | 59.5 |
| 4 | Diisoproplethylamine (1.3 eq.) | 0.93 | 0.93 | 89.3 |

Even when diisopropylethylamine and triethylamine were used as the base, sufficient conversion and selectivity were obtained, so that it was possible to produce the optically active monoxide compound of ((R)-2) with high optical purity.

Even when the addition amount of the base was increased from 1.0 equivalents to 1.3 equivalents, the conversion was slightly improved, and no significant difference was observed in the results.

As compared with the results of Example 9, in the case of using a substrate in a salt form, improvement in the optical purity was observed when diisopropylethylamine or triethylamine was added as a base. It is suggested that the substrate was desalted by the base, and the substrate was subjected to the reaction as a free form. On the other hand, when pyridine was added as a base, influence on the optical purity was hardly observed.
Example 11
Synthesis of (R)-4-[3-(4-benzylpiperidin-1-yl)propionyl]-7-methoxy-2,3,4,5-tetrahydro-1,4-benzothiazepine-1-oxide ((R)-2)
[Chem. 31]
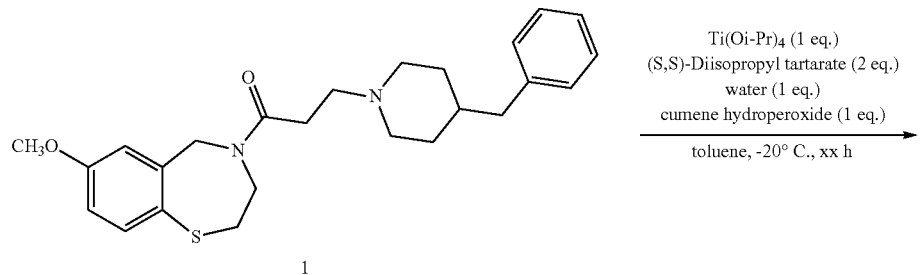
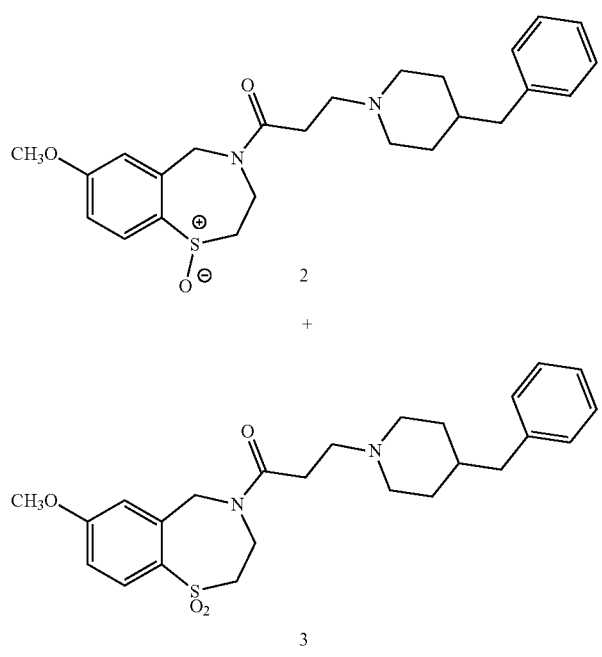

Toluene (10 mL), (S,S)-diisopropyl tartrate (0.908 mL), and titanium tetraisopropoxide (0.642 mL) were added to a 20 mL Schlenk tube under an argon atmosphere, and the mixture was stirred at room temperature for 3 minutes. Subsequently, 4-[3-(4-benzylpiperidin-1-yl)propionyl]-7-methoxy-2,3,4,5-tetrahydro-1,4-benzothiazepine (1) (0.921 g) was added thereto, and the mixture was stirred at room temperature for 3 minutes. Water (0.0390 mL) was added thereto, then the temperature was raised to 50° C., and the mixture was stirred for 2 hours. The reaction mixture was cooled, cumene hydroperoxide (0.397 mL) was then added thereto at −20° C., and the mixture was stirred at the same temperature for 99 hours.

observed by prolonging the reaction time. In addition, no significant effect was observed by reducing the use equivalent of the oxidant from 2.0 equivalents to 1.0 equivalents (equivalent based on the substrate).

Example 12

Synthesis of (R)-4-[3-(4-benzylpiperidin-1-yl)propionyl]-7-methoxy-2,3,4,5-tetrahydro-1,4-benzothiazepine-1-oxide ((R)-2)

[Chem. 32]

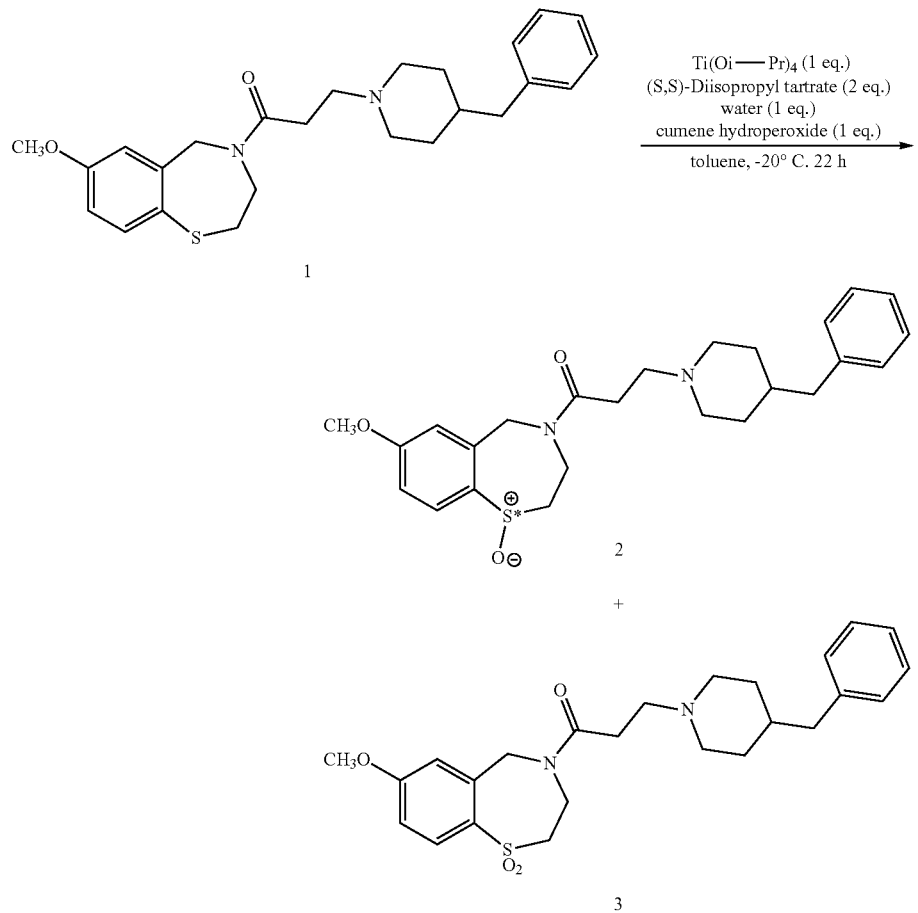

The results were: HPLC conversion: 99%, selectivity of (2)/(3): 93%, enantiomeric excess: 94.5% ee.

As in Example 5, both the conversion and the selectivity were extremely high, and a reaction excellent in the optical purity was achieved, so that an optical isomer of ((R)-2) was obtained with high yield.

As compared with the result of Example 5, a slight improvement in the conversion and optical purity was Toluene (80 mL), (S,S)-diisopropyl tartrate (8.128 g), and titanium tetraisopropoxide (5.136 mL) were added to a 300 mL four-necked flask under an argon atmosphere, and the mixture was stirred at room temperature for 3 minutes. Subsequently, 4-[3-(4-benzylpiperidin-1-yl)propionyl]-7-methoxy-2,3,4,5-tetrahydro-1,4-benzothiazepine (1) (7.367 g) was added thereto, and the mixture was stirred at room temperature for 3 minutes. Water (0.312 mL) was added thereto, then the temperature was raised to 50° C., and the mixture was stirred for 2 hours. The reaction mixture was cooled, cumene hydroperoxide (3.301 mL) was then added thereto at −20° C., and the mixture was stirred at the same temperature for 22 hours.

The results were: HPLC conversion: 97%, selectivity of (2)/(3): 95%, enantiomeric excess: 94.5% ee.

The reaction was further scaled-up than in Example 11, but as in Example 5, both the conversion and the selectivity were extremely high, and a reaction excellent in the optical purity was achieved, so that an optical isomer of ((R)-2) was obtained with high yield.

Example 13

Synthesis of (R)-4-[3-(4-benzylpiperidin-1-yl)propionyl]-7-methoxy-2,3,4,5-tetrahydro-1,4-benzothiazepine-1-oxide ((R)-2)

[Chem. 33]

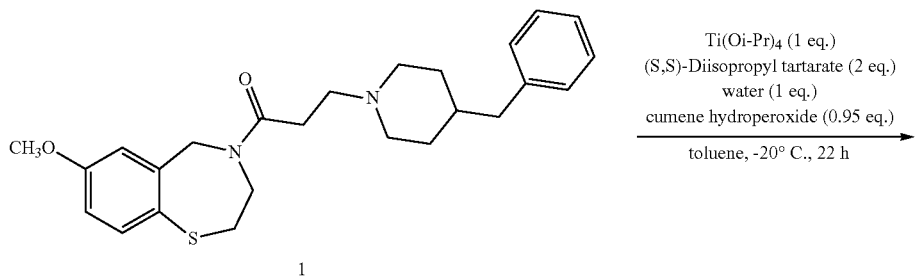

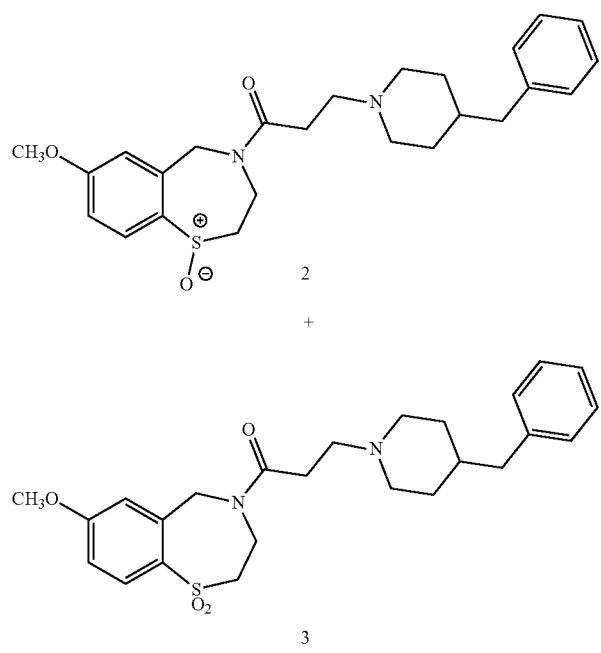

Toluene (10 mL), (S,S)-diisopropyl tartrate (0.908 mL), and titanium tetraisopropoxide (0.642 mL) were added to a 20 mL Schlenk tube under an argon atmosphere, and the mixture was stirred at room temperature for 3 minutes. Subsequently, 4-[3-(4-benzylpiperidin-1-yl)propionyl]-7-methoxy-2,3,4,5-tetrahydro-1,4-benzothiazepine (1) (0.921 g) was added thereto, and the mixture was stirred at room temperature for 3 minutes. Water (0.0390 mL) was added thereto, then the temperature was raised to 50° C., and the mixture was stirred for 2 hours. The reaction mixture was cooled, cumene hydroperoxide (0.377 mL) was then added thereto at −20° C., and the mixture was stirred at the same temperature for 22 hours.

The results were: HPLC conversion: 96%, selectivity of (2)/(3): 96%, enantiomeric excess: 93.9% ee.

As in Example 12, both the conversion and the selectivity were extremely high, and a reaction excellent in the optical purity was achieved, so that an optical isomer of ((R)-2) was obtained with high yield.

Example 14

Synthesis of (R)-4-[3-(4-benzylpiperidin-1-yl)propionyl]-7-methoxy-2,3,4,5-tetrahydro-1,4-benzothiazepine-1-oxide (R)-mandelate performed 3 times. Toluene (70 mL) and (S,S)-diisopropyl tartrate (8.128 g) were added under an argon gas atmosphere, and then titanium tetraisopropoxide (5.136 mL) was added thereto at 27° C. to 30° C.

4-[3-(4-benzylpiperidin-1-yl)propionyl]-7-methoxy-2,3,4,5-tetrahydro-1,4-benzothiazepine (1) diluted with 5 mL of toluene and ultrapure water (0.312 mL) were added at 30° C. The resulting heterogeneous solution was heated to 50° C. and stirred at 50° C. to 55° C. for 1 hour. The obtained single yellow homogeneous reaction mixture was cooled to −19° C., and cumene hydroperoxide (3.301 g) diluted with 5 mL of toluene was added dropwise at −19° C. to −17° C. The obtain reaction resultant was stirred at −21° C. to −19° C. for 22 hours. The reaction was followed by HPLC. 40 mL of a 20% sodium thiosulfate aqueous solution was added, and the mixture was stirred at 0° C. or lower for 20 minutes. The organic layer was separated, and the aqueous layer was re-extracted with 32 mL of ethyl acetate. 32 mL of 3 mol/L hydrochloric acid and 15 mL of methanol were added to the combined organic layers, and the mixture was stirred at room temperature for 5 minutes. The aqueous layer was separated, and the organic layer was re-extracted with 20 mL of a mixed solvent of water/methanol=3/1. The aqueous layer was mixed, a 3 mol/L aqueous potassium carbonate

[Chem. 34]

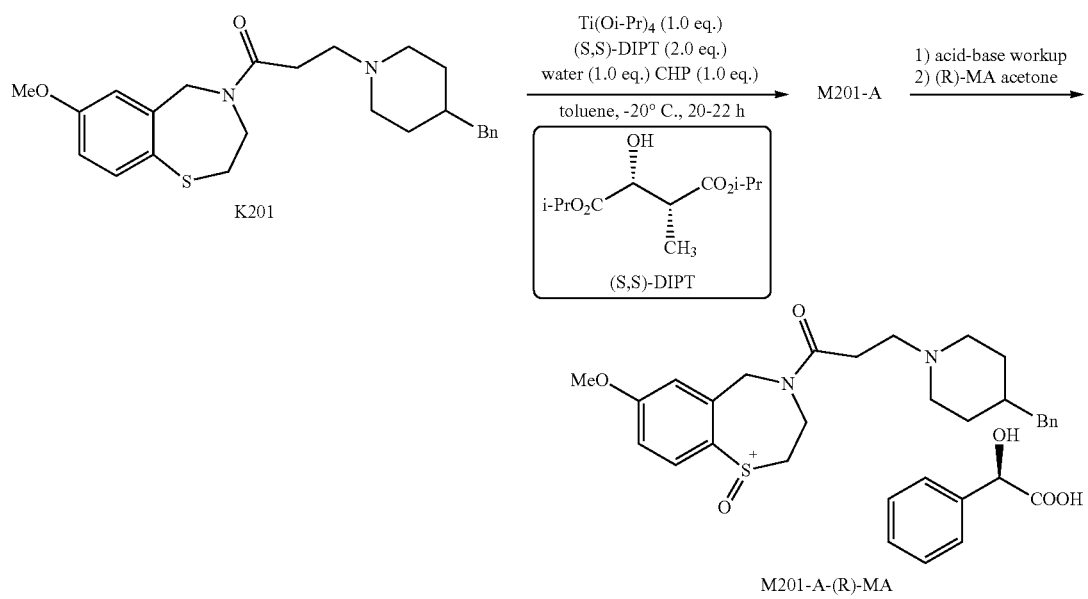

Water (64 mL) and a mixed solvent of hexane/ethyl acetate=1/1 (64 mL) were added to 4-[3-(4-benzylpiperidin-1-yl)propionyl]-7-methoxy-2,3,4,5-tetrahydro-1,4-benzothiazepine (1) hydrochloride (8.00 g), and the mixture was completely dissolved. Sodium carbonate (2.02 g) was added and the mixture was stirred at room temperature for 10 min. The organic layer was separated, and an aqueous layer was extracted twice with a mixed solvent of hexane/ethyl acetate=1/1 (20 mL). All the resulting organic layers were dried over sodium sulfate and concentrated in vacuo with toluene to obtain 4-[3-(4-benzylpiperidin-1-yl)propionyl]-7-methoxy-2,3,4,5-tetrahydro-1,4-benzothiazepine (1).

After the pressure in the 300 mL four-necked flask was reduced, the operation of filling the flask with argon gas was solution, and 30 mL of a THF/toluene mixed solvent were added thereto, and the mixture was stirred at room temperature for 5 minutes. The organic layer was separated, and the aqueous layer was extracted twice with 30 mL of a THF/toluene mixed solvent. The combined organic layers were dried over sodium sulfate.

According to HPLC analysis, ((R)-2) was generated in this reaction mixture at a quantitative yield of 81% and 94.5% ee. After the solvent was substituted with acetone, (R)-mandelic acid (2.61 g) was added at room temperature, and then seed crystals were added, and crystallization was rapidly started. The mixture was stirred at room temperature for 10 minutes, then cooled to 0° C. and aged for 2 hours. The crystals were collected by filtration and washed with cooled acetone.

The obtained solid was dried in vacuo at 60° C. for 4 hours to obtain 7.5377 g of (R)-2-mandelate in 73% yield and 98.1% ee.
High Performance Liquid Chromatography Analysis Conditions (Area Percentage)

Column: Atlantis T3 (manufactured by Waters), 4.6 mm i.d.*100 mm, 5 m 7.31 (m, 3H), 7.31-7.39 (m, 2H), 7.56 (d, J=7.5 Hz, 2H), 7.60 (d, J=8.5 Hz, 0.5×1 H), 7.65 (d, J=8.5 Hz, 0.5×1 H).

Example 15

Synthesis of (R)-4-[3-(4-benzylpiperidin-1-yl)propionyl]-7-methoxy-2,3,4,5-tetrahydro-1,4-benzothiazepine-1-oxide hydrochloride

[Chem. 35]

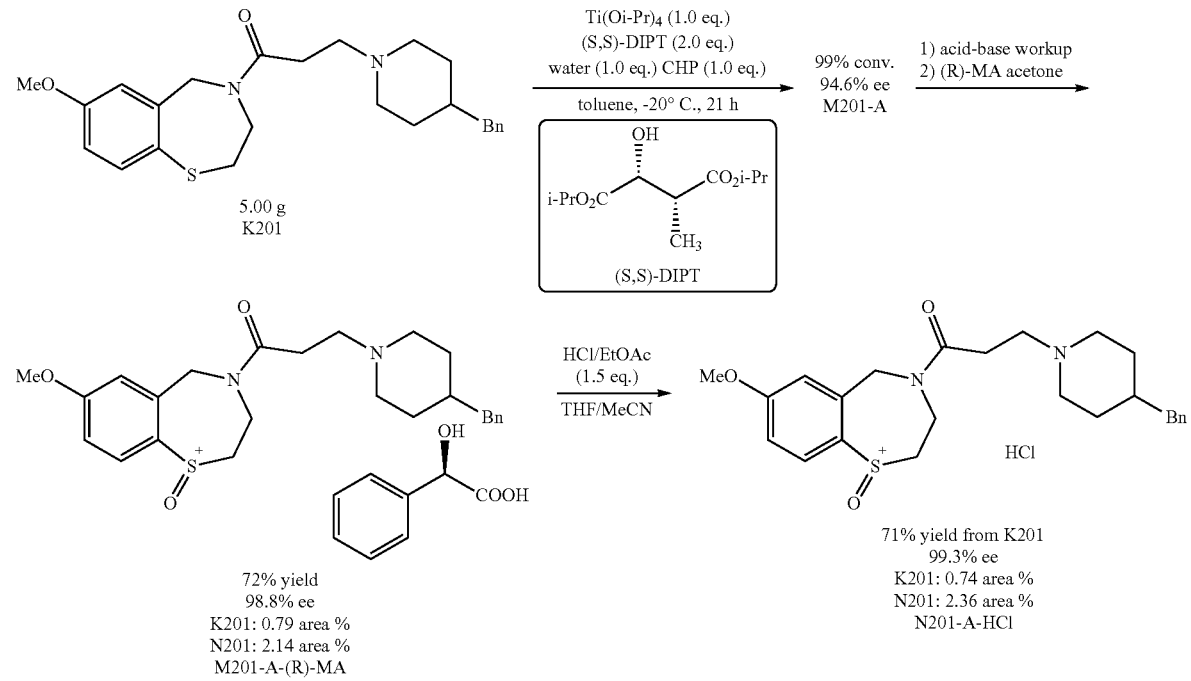

UV detection wavelength: 210 nm
Mobile phase: 0.1 v/v % phosphoric acid/acetonitrile for high performance liquid chromatography=58/42
Flow rate: 1.0 mL/min
Column temperature: 40° C.
Retention time: 1.6 min. (2), 2.1 min. (3), 3.7 min. (1)
High Performance Liquid Chromatography Analysis Conditions (Optical Purity)
Column: CHIRALPAK IC (manufactured by Daicel Corporation), 4.6 mm i.d. * 250 mm, 5 m
UV detection wavelength: 245 nm
Mobile phase: acetonitrile/methanol/diethylamine for high performance liquid chromatography=900/100/1
Flow rate: 1.0 mL/min
Column temperature: 40° C.
Retention time: 5.0 min. (1), 5.6 min. (3), 9.8 min. ((R)-2), 12.5 min. ((S)-2)
The analysis results by nuclear magnetic resonance were as follows.
[Compound Data (R)-2•(R)-MA]

$^1$H NMR (500 MHz, CDCl$_3$, observed as two rotamers whose ratio is 50 to 50) 1.26-1.51 (m, 2H), 1.51-1.76 (m, 3H), 2.23-2.99 (m, 7H), 3.00-3.49 (m, 6H), 3.74-3.85 (m, 1H), 3.80 (s, 0.5×3 H), 3.87 (s, 0.5×3 H), 4.15-4.75 (m, 3H), 4.86-5.15 (m, 1H), 4.98 (s, 1H), 6.80 (dd, J=8.5, 2.0 Hz, 0.5×1 H), 6.85 (dd, J=8.5, 2.0 Hz, 0.5×1 H), 6.99 (dd, J=6.0, 2.5 Hz, 1H), 7.02-7.11 (m, 2H), 7.16-7.23 (m, 1H), 7.23-

Water (40 mL) and a mixed solvent of hexane/ethyl acetate=1/1 (40 mL) were added to 4-[3-(4-benzylpiperidin-1-yl)propionyl]-7-methoxy-2,3,4,5-tetrahydro-1,4-benzothiazepine (1) hydrochloride (5.00 g), and the mixture was completely dissolved. Sodium carbonate (1.26 g) was added and the mixture was stirred at room temperature for 10 min. The organic layer was separated, and an aqueous layer was extracted twice with a mixed solvent of hexane/ethyl acetate=1/1 (10 mL). All the resulting organic layers were dried over sodium sulfate and concentrated in vacuo with toluene to obtain 4-[3-(4-benzylpiperidin-1-yl)propionyl]-7-methoxy-2,3,4,5-tetrahydro-1,4-benzothiazepine (1). After the pressure in the 200 mL four-necked flask was reduced, the operation of filling the flask with argon gas was performed 3 times. Toluene (40 mL) and (S,S)-diisopropyl tartrate (5.081 g) were added under an argon gas atmosphere, and then titanium tetraisopropoxide (3.082 mL) was added thereto at 23° C. to 27° C. 4-[3-(4-benzylpiperidin-1-yl)propionyl]-7-methoxy-2,3,4,5-tetrahydro-1,4-benzothiazepine (1) diluted with 5 mL of toluene and ultrapure water (0.195 mL) were added at 26° C. to 28° C. The resulting heterogeneous solution was heated to 50° C. and stirred at 50° C. to 53° C. for 30 minutes. The obtained single yellow homogeneous reaction mixture was cooled to −19° C., and cumene hydroperoxide (2.063 g) diluted with 5 mL of toluene was added dropwise at −19° C. to −18° C. The obtain reaction resultant was stirred at −20° C. to −19° C. for 21 hours. The reaction was followed by HPLC. 25 mL of a 20% sodium thiosulfate aqueous solution was added, and the mixture was stirred at 0° C. or lower for 10 minutes. The organic layer was separated, and the aqueous layer was re-extracted with 20 mL of ethyl acetate. 20 mL of 3 mol/L hydrochloric acid and 12.5 mL of methanol were added to the combined organic layers, and the mixture was stirred at room temperature for 10 minutes. The aqueous layer was separated, and the organic layer was re-extracted with 10 mL of a mixed solvent of water/methanol=3/1. The aqueous layer was mixed, a 3 mol/L aqueous potassium carbonate solution, and 22.5 mL of a THF/toluene mixed solvent were added thereto, and the mixture was stirred at room temperature for 5 minutes. The organic layer was separated, and the aqueous layer was extracted twice with 15 mL of a THF/toluene mixed solvent. The combined organic layers were dried over sodium sulfate.

According to HPLC analysis, (R)-2 was generated in this reaction mixture at a quantitative yield of 86% and 94.6% ee. After substituting the solvent with acetone, the temperature was raised to 56° C., (R)-mandelic acid (1.65 g) was added, and then the mixture was stirred at the same temperature for 1 minute. The mixture was cooled to room temperature, and the resulting crystals were aged for another 3 hours.

The crystals were collected by filtration and washed with cooled acetone. The obtained solid was dried in vacuo at 60° C. for 2 hours to obtain 4.28 g of (R)-2-mandelate in 72% yield and 98.8% ee.

(R)-2•mandelate (3.00 g) was suspended in 24 mL of a THF/acetonitrile=3/1 mixed liquid. 1.52 mL of 4 mol/L ethyl acetate hydrochloride solution was added dropwise at 22° C. to 28° C., and the mixture was stirred at room temperature for 1 hour. The mixture was cooled to 0° C. and stirred for additional 2 hours. The resulting solid was collected by filtration, washed with 16 mL of THF cooled, and dried overnight in vacuo at 50° C. to obtain 2.38 g of (R)-2-hydrochloride in 98% yield and 99.3% ee.

Example 16

Synthesis of (R)-4-[3-(4-benzylpiperidin-1-yl)propionyl]-7-methoxy-2,3,4,5-1,4-benzothiazepine-1-oxide p-toluenesulfonate THF (6.3 mL) was added to (R)-4-[3-(4-benzylpiperidin-1-yl)propionyl]-7-methoxy-2-3-4-5-tetrahydro-1,4-benzothiazepine-1-oxide (0.700 g), and the mixture was completely dissolved. p-toluenesulfonic acid monohydrate (0.333 g) was added thereto, seed crystals were added thereto, and then the mixture was stirred at room temperature for 19 hours. The mixture was cooled to 0° C. and stirred for another 1 hour. The resulting solid was collected by filtration, washed with 6 mL of cooled THF, and dried in vacuo at 50° C. overnight to obtain 0.941 g of (R)-2-p-toluenesulfonate in 93% yield.

The analysis results by nuclear magnetic resonance were as follows.

[Compound Data (R)-2•p-TsOH] $^1$H NMR (500 MHz, CDCl$_3$, observed as two rotamers whose ratio is 56 to 44) •1.65-1.82 (m, 4H), 2.40 (s, 3H), 2.47-2.71 (m, 4H), 2.81-3.17 (m, 2H), 3.18-3.47 (m, 6H), 3.80 (s, 0.56×3 H), 3.89 (s, 0.44×3 H), 4.03-4.16 (m, 0.56×1 H), 4.24-4.78 (m, 0.56×2 H, 0.44×3 H), 4.97 (d, J=14.0 Hz, 0.56×1 H), 5.21 (d, J=16.0 Hz, 0.44×1 H), 6.70-6.92 (m, 1H), 7.00 (m, 0.56×1 H), 7.04-7.13 (m, 2H), 7.19-7.42 (m, 0.56×6 H, 0.44×7 H), 7.57-7.67 (m, 1H), 7.80 (d, J=8.0 Hz, 2H), 10.50 (bs, 0.56×1 H), 10.58 (bs, 0.44×1 H).

Test Example 1

Moisture absorption property test of (R)-4-[3-(4-benzylpiperidin-1-yl)propionyl]-7-methoxy-2,3,4,5-tetrahydro-1,4-benzothiazepine-1-oxide salt A dynamic vapor sorption (DVS) was measured for hydrochloride, p-toluenesulfonate, and (R)-mandelate of (R)-4-[3-(4-benzylpiperidin-1-yl)propionyl]-7-methoxy-2,3,4,5-tetrahydro-1,4-benzothiazepine-1 oxide, and the moisture absorption properties thereof were examined.

As a result, deliquescence due to moisture absorption was observed in hydrochloric acid (FIG. 1).

In addition, although p-toluenesulfonate absorbed less moisture than hydrochloride, deliquescence was observed (FIG. 2). On the other hand, no moisture absorption was observed in mandelate (FIG. 3).

INDUSTRIAL APPLICABILITY (R)-4-[3-(4-benzylpiperidin-1-yl)propionyl]-7-methoxy-2,3,4,5-tetrahydro-1,4-benzothiazepine-1-oxide or a salt thereof produced by the method of the present invention slowly increases heart rate and blood pressure, and is useful as a therapeutic or preventive agent for atrial fibrillation or heart failure, and therefore the present invention has industrial applicability in the pharmaceutical field.

The invention claimed is:

1. A method for producing an optically active compound of the Formula (IV) or a salt thereof,

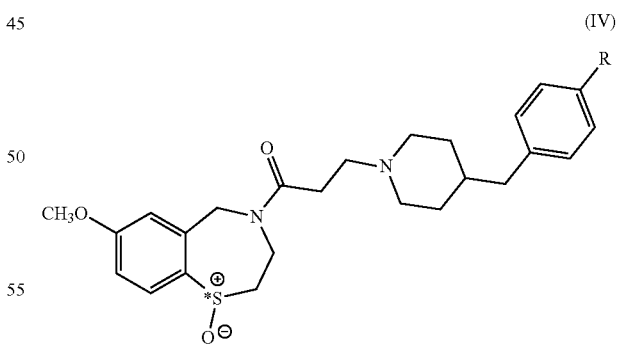

(IV)

wherein * indicates the presence of optical isomers, and R represents a hydrogen atom or a hydroxyl group, wherein the method comprises the following process:

a process of allowing a compound of the Formula (III) or a salt thereof to react with a reactant containing a titanium compound, a chiral diol compound, and water, and an oxidant in a solvent,

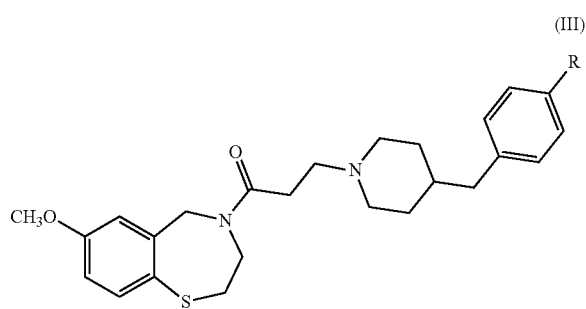

wherein R represents a hydrogen atom or a hydroxyl group.

2. The method according to claim 1, wherein in the Formula (III) and Formula (IV), R is a hydrogen atom.

3. The method according to claim 1, wherein the compound of the Formula (III) or the salt thereof is the compound of Formula (III).

4. The method according to claim 1, wherein the compound of the Formula (III) or the salt thereof is a hydrochloride, fumarate, mandelate, or sulfonate of the compound of the Formula (I).

5. The method according to claim 1, wherein the titanium compound is titanium tetraisopropoxide.

6. The method according to claim 1, wherein the diol compound is tartaric acid diester having the following Formula (V-a) or (V-b):

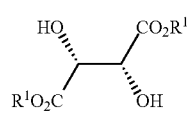

wherein $R^1$ represents an optionally substituted $C_{2-6}$ alkyl group or benzyl, or

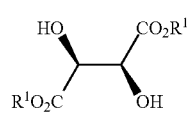

wherein $R^1$ is as defined above.

7. The method according to claim 6, wherein the tartaric acid diester of the Formula (V-a) or (V-b) is tartaric acid diester selected from the group consisting of diethyl tartarate, diisopropyl tartarate, and dibenzyl tartarate.

8. The method according to claim 1, wherein the oxidant is a t-butyl hydroperoxide aqueous solution or cumene hydroperoxide.

9. The method according to claim 8, wherein the oxidant is cumene hydroperoxide.

10. The method according to claim 1, wherein the solvent is a solvent selected from the group consisting of toluene, chloroform, and ethyl acetate.

11. The method according to claim 10, wherein the solvent is toluene.

12. The method according to claim 1, wherein the optically active compound is an (R)-form optically active compound, and the chiral diol compound is (S,S)-tartaric acid diester having the Formula (V-a).

13. The method according to claim 1, wherein the optically active compound is an (S)-form optically active compound, and the chiral diol compound is (R,R)-tartaric acid diester having the Formula (V-b).

14. A method for producing hydrochloride of an optically active compound of the Formula (VIII),

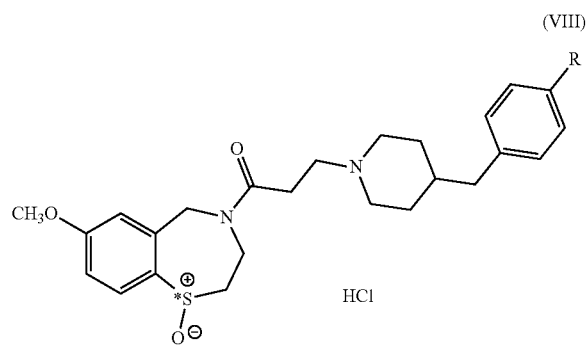

wherein, * indicates the presence of optical isomers, and R represents a hydrogen atom or a hydroxyl group,
the method comprises the following processes:
a process of allowing a salt selected from the group consisting of fumarate, mandelate, and sulfonate of a compound of the Formula (III) to react with a reactant containing a titanium compound, a chiral diol compound, and water, and an oxidant in a solvent;

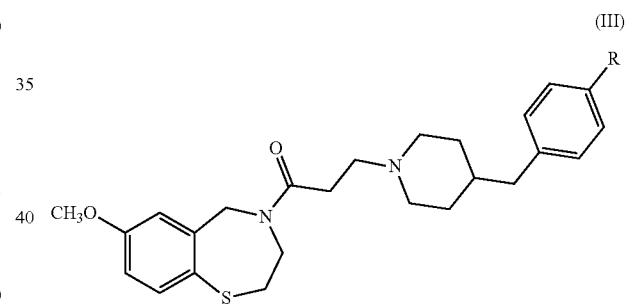

wherein R represents a hydrogen atom or a hydroxyl group,
a process of isolating a salt selected from the group consisting of fumarate, mandelate, and sulfonate of an optically active compound of the Formula (IV), which is a product obtained in the previous process,

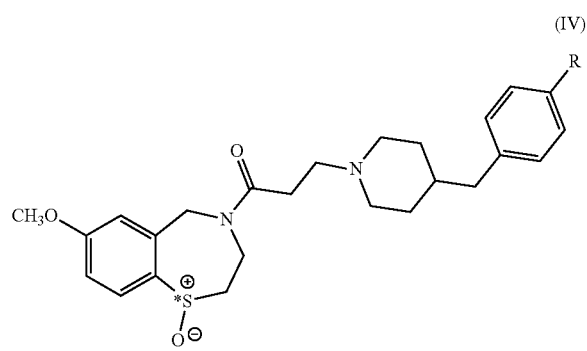

wherein, * indicates the presence of optical isomers, and R represents a hydrogen atom or a hydroxyl group; and a process of converting the salt.

15. The method according to claim 14, wherein the salt selected from the group consisting of fumarate, mandelate, and sulfonate is mandelate.

16. The method according to claim 14, wherein R is a hydrogen atom.

17. The method according to claim 14, wherein the optically active compound is an (R)-form optically active compound, and the chiral diol compound is (S,S)-tartaric acid diester of the Formula (V-a),

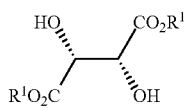

(V-a)

wherein $R^1$ represents an optionally substituted $C_{2-6}$ alkyl group or benzyl.

18. The method according to claim 14, wherein the optically active compound is an (S)-form optically active compound, and the chiral diol compound is (R,R)-tartaric acid diester of the Formula (V-b),

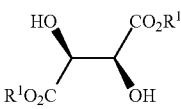

(V-b)

wherein $R^1$ represents an optionally substituted $C_{2-6}$ alkyl group or benzyl.

* * * * *